US010786381B2

(12) United States Patent
Paulos et al.

(10) Patent No.: US 10,786,381 B2
(45) Date of Patent: Sep. 29, 2020

(54) ELASTIC BRACE ASSEMBLY AND METHODS OF USE

(71) Applicants: THE LONNIE AND SHANNON PAULOS TRUST (AS AMENDED AND RESTATED), Salt Lake City, UT (US); Kim A. Nelson, Salt Lake City, UT (US)

(72) Inventors: Lonnie E. Paulos, Salt Lake City, UT (US); Kim A. Nelson, Salt Lake City, UT (US)

(73) Assignee: KNEE X BRACE LLC, Salt Lake City, UT (US)

( * ) Notice: Subject to any disclaimer, the term of this patent is extended or adjusted under 35 U.S.C. 154(b) by 549 days.

(21) Appl. No.: 15/406,738

(22) Filed: Jan. 15, 2017

(65) Prior Publication Data
US 2017/0189218 A1 Jul. 6, 2017

Related U.S. Application Data

(63) Continuation of application No. 14/447,703, filed on Jul. 31, 2014, now Pat. No. 9,554,934, which is a
(Continued)

(51) Int. Cl.
*A61F 5/01* (2006.01)
*A61F 5/37* (2006.01)

(52) U.S. Cl.
CPC .......... *A61F 5/0109* (2013.01); *A61F 5/0102* (2013.01); *A61F 5/0111* (2013.01);
(Continued)

(58) Field of Classification Search
CPC .... A61F 5/0102; A61F 5/0123; A61F 5/0125; A61F 2005/0167; A61F 2005/0139
See application file for complete search history.

(56) References Cited

U.S. PATENT DOCUMENTS 2,603,786 A * 7/1952 Haines ............... A41D 13/0568
2/24
3,669,105 A 6/1972 Castiglia
(Continued)

FOREIGN PATENT DOCUMENTS

EP 1462072 9/2004
JP 01150916 10/1989
(Continued)

OTHER PUBLICATIONS

Christopher Geiser, Kristian M. O'Connor, Jennifer E. Earl, Effects of Isolated Hip Abductor Fatigue on Frontal Plane Knee Mechanics, Marquette University e-Publications@Marquette, Health Sciences Faculty Research and Publications, College of Health Sciences, Medicine and Science in Sports and Exercise, vol. 42, No. 3, Mar. 2010, pp. 535-545.
(Continued)

*Primary Examiner* — Ophelia A Hawthorne
(74) *Attorney, Agent, or Firm* — John J. Brooks, III; John Brooks Law LLC

(57) ABSTRACT

Example embodiments of the brace assembly utilize an elastic cross strap attached to mounting facilities about a joint to provide progressive resistance to the extension, flexion or other movement of body parts about the joint. In some embodiments for a knee joint, the brace assembly provides a progressive resisting force to resist hyperextension of the knee. Some embodiments of the assembly may be able to accommodate different joints, different size wearer's of the assembly and different tension settings such as for athletes during competition. Some embodiments of the brace assembly may be used bilaterally and can be made without metal bracing to comply with the requirements of some sports. Some embodiments of the mounting facilities may have through holes.

22 Claims, 22 Drawing Sheets

Related U.S. Application Data continuation-in-part of application No. 13/188,506, filed on Jul. 22, 2011, now Pat. No. 8,808,211, and a continuation-in-part of application No. 12/993,258, filed on Nov. 18, 2010, now Pat. No. 8,852,133, and a continuation-in-part of application No. 13/541,796, filed as application No. PCT/US2009/046183 on Jun. 3, 2009, now Pat. No. 9,320,634, said application No. 13/188,506 is a continuation-in-part of application No. PCT/US2009/067152, filed on Dec. 8, 2009, which is a continuation-in-part of application No. PCT/US2009/046183, filed on Jun. 3, 2009, said application No. 13/188,506 is a continuation-in-part of application No. 12/993,258, filed on Nov. 18, 2010, now Pat. No. 8,852,133, said application No. 13/541,796 is a continuation-in-part of application No. 12/993,258, filed on Nov. 18, 2010, now Pat. No. 8,852,133, and a continuation-in-part of application No. 13/188,506, filed on Jul. 22, 2011, now Pat. No. 8,808,211.

(60) Provisional application No. 61/864,674, filed on Aug. 12, 2013, provisional application No. 61/148,973, filed on Feb. 1, 2009, provisional application No. 61/058,555, filed on Jun. 3, 2008, provisional application No. 61/262,723, filed on Nov. 19, 2009, provisional application No. 61/263,737, filed on Nov. 23, 2009, provisional application No. 61/504,341, filed on Jul. 5, 2011, provisional application No. 61/466,909, filed on Mar. 23, 2011.

(52) U.S. Cl.
CPC .............. *A61F 5/0125* (2013.01); *A61F 5/37* (2013.01); *A61F 5/3723* (2013.01); *A61F 2005/0179* (2013.01)

(56) References Cited

U.S. PATENT DOCUMENTS

| | | | |
|---|---|---|---|
| 4,240,414 A | 12/1980 | Theisler | |
| 4,294,238 A | 10/1981 | Woodford | |
| 4,556,054 A | 12/1985 | Paulseth | |
| 4,702,234 A | 10/1987 | Hutjens et al. | |
| 4,817,588 A | 4/1989 | Bledsoe | |
| 4,854,308 A * | 8/1989 | Drillio | A61F 5/0123 602/16 |
| 5,063,916 A | 11/1991 | France et al. | |
| 5,277,698 A * | 1/1994 | Taylor | A61F 5/0123 602/16 |
| 5,399,153 A | 3/1995 | Caprio, Jr. et al. | |
| 5,417,647 A | 5/1995 | Down | |
| 5,512,039 A * | 4/1996 | White | A61F 5/0106 602/26 |
| 5,554,105 A | 9/1996 | Taylor | |
| 5,873,848 A | 2/1999 | Fulkerson | |
| 5,891,079 A | 4/1999 | Barnes | |
| 6,368,297 B1 | 4/2002 | Smits | |
| 7,198,610 B2 * | 4/2007 | Ingimundarson | A61F 5/0123 602/16 |
| 7,871,388 B2 | 1/2011 | Brown | |
| 7,959,591 B2 | 6/2011 | Powers et al. | |
| 8,007,457 B2 | 8/2011 | Taylor et al. | |
| 8,167,829 B2 | 5/2012 | Sterling et al. | |
| 8,905,956 B2 | 12/2014 | Waeger | |
| 9,168,167 B2 | 10/2015 | Brown | |
| 9,452,078 B2 | 9/2016 | Waeger | |
| 9,554,934 B2 * | 1/2017 | Paulos | A61F 5/0125 |
| 2002/0010410 A1 * | 1/2002 | Steponovich | A61F 5/0106 602/26 |
| 2003/0204156 A1 | 10/2003 | Nelson et al. | |
| 2003/0232701 A1 | 12/2003 | Latella, Jr. | |
| 2004/0116260 A1 | 6/2004 | Drennan | |
| 2005/0197607 A1 | 9/2005 | Brown | |
| 2006/0000478 A1 | 1/2006 | Taylor | |
| 2006/0089583 A1 | 4/2006 | Reinhardt | |
| 2008/0066272 A1 | 3/2008 | Hammerslag et al. | |
| 2008/0083055 A1 | 4/2008 | Onda et al. | |
| 2009/0062704 A1 | 3/2009 | Brown et al. | |
| 2009/0090027 A1 | 4/2009 | Baudouin et al. | |
| 2010/0069802 A1 | 3/2010 | Motyer | |
| 2010/0088803 A1 | 4/2010 | Orloff et al. | |
| 2011/0009793 A1 | 1/2011 | Lucero et al. | |
| 2011/0213283 A1 | 9/2011 | Brown | |
| 2012/0316483 A1 | 12/2012 | Waeger | |
| 2015/0040286 A1 | 2/2015 | Schultz et al. | |
| 2015/0094634 A1 | 4/2015 | Waeger | |

FOREIGN PATENT DOCUMENTS

| | | | |
|---|---|---|---|
| KR | 100742181 | 7/2007 | |
| WO | WO1988001855 | 3/1988 | |
| WO | WO-9400082 A1 * | 1/1994 | ........... A61F 13/062 |
| WO | WO199400082 | 1/1994 | |
| WO | WO2007020372 | 2/2007 | |

OTHER PUBLICATIONS

Sue D. Barber-Westin, Stephaine T. Smith, Thomas Campbell, and Frank R. Noyes, the Drop-Jump video ScreeningTest: Retention of Improvement in Neuromuscular Control in Female Volleyball Players, Journal of Strength and Conditioning Research 2010 National Strength and Conditioning Association, vol. 0, No. 0, Month 2010, 8 pages.

Cale A. Jacobs, Timothy L. Uhl, Carl G. Mattacola, Robet Shapiro, William S. Rayens, Hip Abductor Function and Lower Extremity Landing Kinematics: Sex Differences, Journal of Athletic Training 2007; 42 (1)1:76-83 by the National Athletic Trainers' Association, Inc. www.journalofathletictraining.org, 8 pages.

Gregory D. Myer, Kevin R. Ford, Joseph P. Palumbo, and Timothy E. Hewett, Neuromuscular Training Improves Performance and Lower-Extremity Biomechanics in Female Athletes, Journal of Strength and Conditioning Research, 2005, 19(1), 51-60, 2005 National Strength & Conditioning Association, 10 pages.

WIPO, Park, Se Young, International Searching Authority, International Search Report and the Written Opinion of the International Searching Authority of parent PCT Application No. PCT/US09/67152 to Lonnie E Paulos, 9 pages, dated Jul. 26, 2010, Korea.

WIPO, Moon Song, John, International Search Report and the Written Opinion of the International Searching Authority, Korean Intellectual Property Office for PCT Application No. PCT/US2009/046183 to Lonnie E. Paulos, 11 pages, dated Jan. 18, 2010, Korea.

USPTO, Lewis, Kim M, USPTO Office Action for U.S. Appl. No. 12/993,258, 14 pages, dated Aug. 19, 2013, USA.

USPTO, Lewis, Kim M., U.S. Appl. No. 12/993,258, Final Office Action dated Feb. 4, 2014, 9 pages, US.

USPTO, Lewis, Kim M., U.S. Appl. No. 12/993,258, Notice of Allowance dated Jun. 4, 2014, 17 pages, US.

USPTO, Hawthorne, Ophelia Althea, USPTO Office Action for U.S. Appl. No. 13/188,506, 17 pages, dated Aug. 5, 2013, USA.

USPTO, Hawthorne, Ophelia Althea, USPTO Office Action for U.S. Appl. No. 13/188,506, 17 pages, dated Sep. 3, 2013, USA.

USPTO, Hawthorne, Ophelia Althea, U.S. Appl. No. 13/188,506, Final Office Action dated Jan. 15, 2014, 11 pages, US.

USPTO, Hawthorne, Ophelia Althea, USPTO, U.S. Appl. No. 13/188,506, Notice of Allowance, dated Apr. 11, 2014, 11 pages, US.

USPTO, Hawthorne, Ophelia Althea, USPTO, U.S. Appl. No. 14/447,703, Non-Final Office Action, dated Dec. 14, 2015, 18 pages, USA.

USPTO, Hawthorne, Ophelia Althea, USPTO, U.S. Appl. No. 14/447,703, Final Office Action, dated Jun. 27, 2016, 12 pages, US.

USPTO, Hawthorne, Ophelia Althea, USPTO, U.S. Appl. No. 14/447,703, Notice of Allowance, dated Sep. 21, 2016, 3 pages, USA.

(56) References Cited

OTHER PUBLICATIONS

USPTO, Hawthorne, Ophelia, Althea, U.S. Appl. No. 13/541,796, Non-Final Office Action, dated Dec. 16, 2014, 15 pages, US.
USPTO, Hawthorne, Ophelia, Althea, U.S. Appl. No. 13/541,796, Final Office Action, dated Jul. 29, 2015, 19 pages, US.
USPTO, Hawthorne, Ophelia, Althea, Application No. 13/541,796, Notice of Allowance, dated Oct. 29, 2015, 13 pages, US.
Jeremy Paul Loenneke and Thomas Joseph Pujol, The Use of Occlusion Traiing to Product Muscle Hypertrophy, National Strength and Conditioning Association, Strength and Conditioning Journal, vol. 00, No. 0, 2009, USA.
Click Medical, Click Medical Solutions Guide, 2009, USA.
USPTO, Hawthorne, Ophelia Althea, U.S. Appl. No. 15/423,851, Office Action dated May 14, 2019, 19 pages, US.
USPTO, Nelson, Keri Jessica, U.S. Appl. No. 15/195,618, Office Action dated Jun. 20, 2019, 10 pages, US.
USPTO, Nelson, Keri Jessica, U.S. Appl. No. 13/195,608, Office Action, dated Dec. 21, 2018, 8 pages, US.
USPTO, Hawthorne, Ophelia Althea, U.S. Appl. No. 15/423,851, Office Action dated Nov. 26, 2019, 20 pages. US.
USPTO, Hawthorne, Ophelia Althea, U.S. Appl. No. 15/423,851, Notice of Allowance dated Feb. 7, 2020, 8 pages, US.

\* cited by examiner

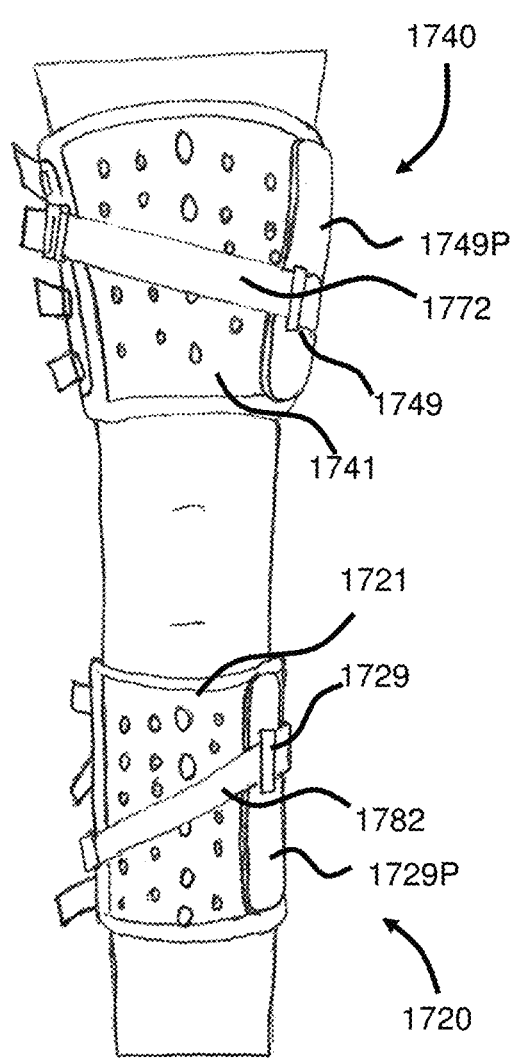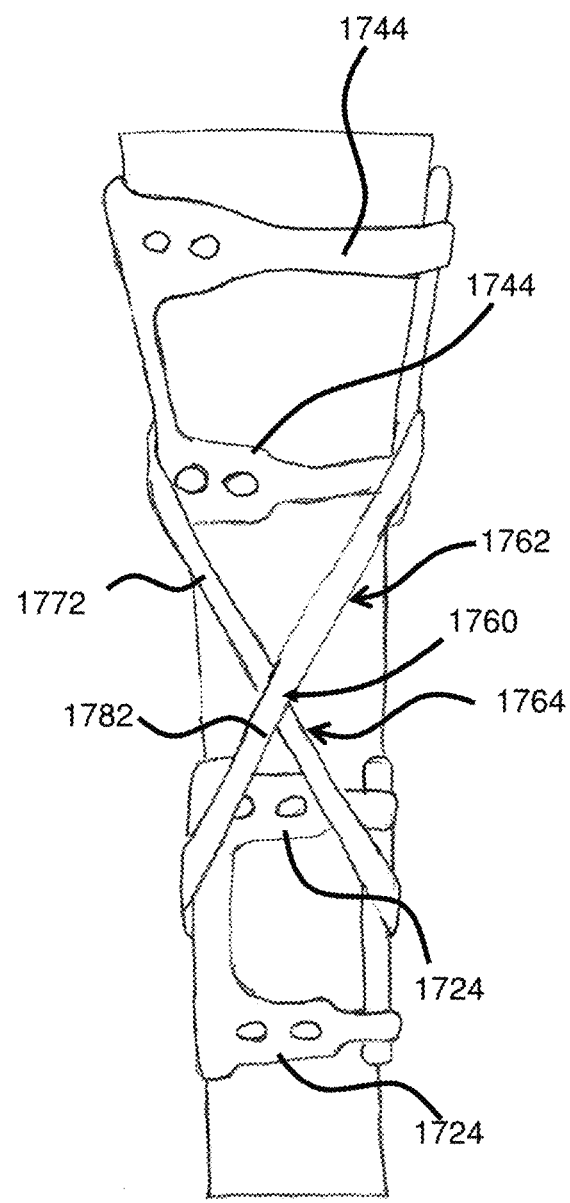
FIG. 17C
FIG. 17D

ELASTIC BRACE ASSEMBLY AND METHODS OF USE

CROSS-REFERENCE TO RELATED APPLICATIONS

This application is a Continuation of pending U.S. patent application Ser. No. 14/447,703 filed Jul. 31, 2014; U.S. patent application Ser. No. 14/447,703 claims benefit of U.S. Pat. App. No. 61/864,674 filed Aug. 12, 2013; U.S. patent application Ser. No. 14/447,703 is a Continuation in Part App. of U.S. patent application Ser. No. 12/993,258 filed Nov. 18, 2010, U.S. patent application Ser. No. 12/993,258 is the U.S. National Stage App. of International App. No. PCT/US09/46183 filed Jun. 3, 2009, International App. No. PCT/US09/46183 claims benefit of U.S. Pat. App. No. 61/148,973 filed Feb. 1, 2009 and International App. No. PCT/US09/46183 claims benefit of U.S. Pat. App. No. 61/058,555 filed Jun. 3, 2008; this application is a Continuation in Part App. of U.S. patent application Ser. No. 13/188,506 filed Jul. 22, 2011, U.S. patent application Ser. No. 13/188,506 claims benefit of U.S. Pat. App. No. 61/466,909 filed Mar. 23, 2011, U.S. patent application Ser. No. 12/188,506 is a Continuation in Part App. of International App. No. PCT/US09/67152 filed Dec. 8, 2009, International App. No. PCT/US09/67152 claims benefit of U.S. Pat. App. No. 61/262,723 filed Nov. 19, 2009, International App. No. PCT/US09/67152 claims benefit of U.S. Pat. App. No. 61/263,737 filed Nov. 23, 2009, International App. No. PCT/US09/67152 is a Continuation in Part App. of International App. No. PCT/US09/46183 filed Jun. 3, 2009, International App. No. PCT/US09/46183 claims benefit of U.S. Pat. App. No. 61/058,555 filed Jun. 3, 2008, International App. No. PCT/US09/46183 claims benefit of U.S. Pat. App. No. 61/148,973 filed Feb. 1, 2009, U.S. patent application Ser. No. 12/188,506 is a Continuation in Part App. of U.S. patent application Ser. No. 12/993,258 filed Nov. 18, 2010, U.S. patent application Ser. No. 12/993,258 is the U.S. National Stage App. of International App. No. PCT/US09/46183, International App. No. PCT/US09/46183 claims benefit of U.S. Pat. App. No. 61/058,555 filed Jun. 3, 2008 and International App. No. PCT/US09/46183 claims benefit of U.S. Pat. App. No. 61/148,973 filed Feb. 1, 2009; this application is a Continuation in Part App. of U.S. patent application Ser. No. 13/541,796 filed Jul. 5, 2012, U.S. patent application Ser. No. 13/541,796 claims benefit of U.S. Pat. App. No. 61/504,341 filed Jul. 5, 2011, U.S. patent application Ser. No. 13/541,796 is a Continuation in Part App. of U.S. patent application Ser. No. 13/188,506 filed Jul. 22, 2011, U.S. patent application Ser. No. 13/188,506 is a Continuation in Part App. of International App. No. PCT/US09/67152 filed Dec. 8, 2009, U.S. patent application Ser. No. 13/188,506 claims benefit of U.S. Pat. App. No. 61/466,909 filed Mar. 23, 2011, International App. No. PCT/US09/67152 claims benefit of U.S. Pat. App. No. 61/262,723 filed Nov. 19, 2009, International App. No. PCT/US09/67152 claims benefit of U.S. Pat. App. No. 61/263,737 filed Nov. 23, 2009, International App. No. PCT/US09/67152 is a Continuation in Part App. of International App. No. PCT/US09/46183 filed Jun. 3, 2009, International App. No. PCT/US09/46183 claims benefit of U.S. Pat. App. No. 61/058,555 filed Jun. 3, 2008, International App. No. PCT/US09/46183 claims benefit of U.S. Pat. App. No. 61/148,973 filed Feb. 1, 2009, U.S. patent application Ser. No. 13/541,796 is a Continuation in Part App. of U.S. patent application Ser. No. 12/993,258 filed Nov. 18, 2010, U.S. patent application Ser. No. 12/993,258 is the U.S. National Stage App. of International App. No. PCT/US09/46183, International App. No. PCT/US09/46183 claims benefit of U.S. Pat. App. No. 61/058,555 filed Jun. 3, 2008 and International App. No. PCT/US09/46183 claims benefit of U.S. Pat. App. No. 61/148,973 filed Feb. 1, 2009; and this application incorporates by reference all of the above referenced applications in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

Field of the Invention

Embodiments of the present invention relate to joint braces that can help prevent the hyperextension, flexion or undesirable movement of a joint, and more specifically relates to brace assemblies and methods utilizing an elastic cross strap that assists in preventing undesirable movement of the joint.

Prior Art

Braces are often utilized to support joints when damage, deformation, surgery or the like has caused the joint to be instable. Sports, physical labor and everyday physical movement can create strains and injuries to joints such as the shoulder, elbow, back, wrist, ankle and knee. Specific to the knee, most of the running, jumping, cutting or twisting sports today have the risk of damaging the knee. These injuries frequently involve a tearing the ACL in the knee. Many injures to the knee joint have a mechanism of injury of hyperextension in which the ACL is stretched or torn. Many methods have been employed to prevent this action to the knee and prevent the injury to the ACL. Taping techniques as well as rigid braces have been designed to prevent this condition.

One common method of treatment and prevention for these injures today is the use of the rigid braces. Common to most, if not all, of these devises for use on the knee are, adjustable metal hinges on the medial and lateral side of the knee. Rigid arms on each side connect the hinges to curved thigh and calf pieces or cuffs. A series of Velcro straps attached to these rigid side pieces then wrap around the leg to mount and hold them in place with the cuffs and the hinges. Adjusting the hinge from allowing extension or hyperextension blocks the knee from moving into to these positions quite well.

With respect to these rigid braces however, many sports have rules in which players cannot have any metal or rigid devices on any part of their body to compete due to metal or hard structures that may cause injury to other players. One of these sports is soccer, which is also one of the most popular sports in the world. Additionally, with the introduction of bracing both knees for prevention of injury, the bracing must have a very low profile on the knees to prevent the braces from catching against each other during competition.

Another technique of treating and preventing joint injuries includes taping techniques. While reinforcing joint strength, taping typically does not involve rigid braces that cause problems with sporting rules.

Prior art embodiments of braces having strap elements that cross posterior to the knee joint include U.S. Pat. No. 4,817,588 filed on Jul. 1, 1987 to Gary Bledsoe (Bledsoe) and U.S. Pat. No. 6,368,297 filed on Oct. 22, 1999 to Jan F. A. Smits (Smits) both of which are incorporated by reference in their entirety. Bledsoe discloses a restraining strap network positioned entirely behind the knee that has to cooperate with additional brace elements including hinges and connecting means to connect the brace elements to the wearer's leg. Bledsoe does not disclose embodiments of the strap network extending anterior to the limbs about the joint. Smits discloses a brace having a strap that crosses at the back of the knee that like Bledsoe is entirely behind the knee and has to cooperate with other brace elements. Smits also specifically uses stop portions in a hinge to limit extension of the brace elements. Smits does not disclose limiting extension of the brace with the strap.

SUMMARY OF THE INVENTION

The following summary is included only to introduce some concepts discussed in the Detailed Description below. This summary is not comprehensive and is not intended to delineate the scope of protectable subject matter.

Example embodiments of the elastic brace assembly utilize an elastic cross strap attached to mounting facilities about a joint to limit the extension of limbs about the joint. The cross strap has elastic properties that allow it to provide progressive resistance as the strap is stretched. The elastic cross strap assembly is positioned from a cross origin behind or in the fossa of the joint to attachment points on mounting facilities on either side of the joint such that the assembly provides an opposing tensile force that limits the extension of the mounting facilities and the limbs about a joint.

In example embodiments for other joints, the brace assembly may provide a resisting force that influences appendages about a joint. For example: for an ankle, the brace can be used to prevent dorsiflection, plantar flexion or rolling of the ankle; for a back, the brace can be used to prevent or support bending about the waist; for an elbow, the brace can be used to prevent hyperextension; and for a shoulder, the brace can be used to control movement of the humerus about the shoulder such as to restrict abduction and external rotation.

In example embodiments for a knee joint, the brace assembly provides a resisting force to resist hyperextension of the knee. Some embodiments of the assembly are able to accommodate different joints, different size wearer's of the assembly and different tension settings such as for athletes during competition. Some embodiments of the brace can be used bilaterally and can be made without metal bracing to comply with the requirements of some sports.

Some embodiments of the brace assembly provide an elastic knee brace assembly having an upper mounting facility for positioning the brace assembly about the thigh area of a user's leg, a lower mounting facility for positioning the brace assembly about the shin area of the user's leg, a elastic cross strap having a cross origin, and the cross strap is attachable to the upper and lower mounting facilities whereby the cross strap limits the extension of the upper mounting facility and the lower mounting facility about the joint when the cross origin is positioned posterior to the user's knee.

Some embodiments of the elastic brace assembly comprise an upper mounting facility and a lower mounting facility, at least one elastic cross strap coupled to the upper mounting facility and lower mounting facility and the elastic cross strap further forming a cross origin between the upper and lower mounting facility whereby the cross strap provides a resistance force to an extension of the upper mounting facility and the lower mounting facility from the cross origin when the cross origin is positioned in a fossa of a wearer's joint.

In some embodiments, the upper mounting facility comprises an upper pad and an upper strap configured to wrap around an upper limb of a joint and the lower mounting facility comprising a lower pad and a lower strap configured to wrap around a lower limb of a joint of a wearer.

In some embodiments, the elastic cross strap is coupled to the upper mounting facility at an attachment point lateral or medial to an anterior point of the upper mounting facility and the elastic cross strap is coupled to the upper mounting facility at an attachment point lateral or medial to an anterior point of the upper mounting facility.

In some embodiments, the brace assembly further comprises at least one buckle capable of removably coupling the elastic cross strap to the upper pad or the lower pad and capable of adjustably coupling the elastic cross strap to the upper pad or the lower pad.

In some embodiments, the wearer's joint is a knee joint whereby the elastic cross strap provides the resistance force to the extension of the upper mounting facility and the lower mounting facility from the cross origin when the cross origin is positioned in the popliteal fossa of the knee joint.

In some embodiments, the elastic cross strap is coupled to the upper mounting facility at an attachment point at an anterior point of the upper mounting facility and the elastic cross strap coupled to the upper mounting facility at an attachment point at an anterior point of the upper mounting facility.

In some embodiments, the upper mounting facility comprises an upper pad and an upper strap configured to wrap around an upper limb of a joint and the lower mounting facility comprises a lower pad and a lower strap configured to wrap around a lower limb of a joint of a wearer.

In some embodiments, the upper mounting facility comprising an upper pad and an upper strap configured to wrap around an upper limb of a joint, the lower mounting facility lower pad and a lower strap configured to wrap around a lower limb of a joint of a wearer, the upper strap and the lower strap are made of an elastic material and the upper mounting facility and the lower mounting facility are coupled with a mechanical hinge.

In some embodiments, the inner surface further comprises a plurality of through holes extending through the upper pad and the lower pad to provide further frictional engagement of the upper and lower limb of the wearer.

In some embodiments, the upper strap and the lower strap are made of an elastic material and the upper pad and the lower pad are made of an elastic material.

In some embodiments, the upper pad and the lower pad have an inner surface configured to frictionally engage the upper and lower limb of the wearer and the inner surface having an indentation pattern. In some embodiments, the inner surface further comprises a plurality of through holes extending through the upper pad and the lower pad to provide further frictional engagement of the upper and lower limb of the wearer. In some embodiments, the inner surface further comprises a plurality of strips extending between the through holes to provide the first progressive resistance force.

In some embodiments, the elastic cross strap is configured to provide a dynamic, progressive or configurable resistance force as the resistance force.

In some embodiments the upper mounting facility and the lower mounting facility are not coupled with a mechanical hinge.

Some embodiments of the elastic brace assembly comprise an upper mounting facility and a lower mounting facility, one of the upper mounting facility or the lower mounting facility comprising an elastic pad configured to provide a first progressive resistance force at least one elastic cross strap configured to provide a strap progressive resistance force and the elastic cross strap coupled to the upper mounting facility and lower mounting facility whereby the first progressive resistance force and the strap progressive resistance force provides a combined progressive resistance force to an extension of the upper mounting facility and the lower mounting facility about a wearer's joint. In some embodiments, the inner surface further comprises a plurality of through holes extending through the elastic pad to provide further frictional engagement of the upper and lower limb of the wearer and the inner surface further comprises a plurality of strips extending between the through holes to provide the first progressive resistance force. In some embodiments, the upper mounting facility comprises a first elastic pad configured to provide the first progressive resistance force, the lower mounting facility comprises a second elastic pad configured to provide a second progressive resistance force, the elastic cross strap forms a cross origin between the upper and lower mounting facility and the combined progressive force comprises the first progressive force, the second progressive force and the strap progressive force.

Some embodiments of the elastic brace assembly comprise an upper mounting facility and a lower mounting facility, at least one elastic cross strap coupled to the upper mounting facility and lower mounting facility and the at least one elastic cross strap further forming a cross origin between the upper and lower mounting.

In some embodiments, the elastic cross strap is configured to provide a progressive change in a resistance force on the upper mounting portion and the lower mounting portion.

In some embodiments, the resistance force is a configurable resistance force.

In some embodiments, the resistance force is a progressive resistance force provided by the elastic cross strap comprising a composite of tensile elements.

In some embodiments, the composite of tensile elements comprises a first tensile element having a first tensile strength and a first resting length, a second tensile element having a second tensile strength greater than the first tensile strength and a second resting length longer than the first resting length whereby a first resistance force is provided through a first stretch range up to the second resting length and a second resistance force is provided in a second stretch range beyond the second resting length.

In some embodiments, the resistance force is a configurable resistance force provided by the elastic cross strap being one from a group consisting of: the elastic cross strap having one of a plurality of different lengths, the elastic cross strap having one of a plurality of different tensile elements, the elastic cross strap comprising one of a plurality of elastic materials having different tensile properties, the elastic cross strap comprising an adjustable length of the elastic training portion and a first end of the elastic cross strap having one of a plurality of attachment points on the lower mounting facility defining a lower resistance point and positioning a second end of the elastic cross strap on one of a plurality of attachment points on the upper mounting facility defining an upper resistance point.

Some embodiments of the invention provide an elastic brace assembly comprising an elastic cross strap attached to an upper mounting facility and a lower mounting facility and the elastic cross strap further forming a cross origin between the upper and lower mounting facilities whereby the cross strap provides a resistance force to an extension of the upper mounting facility and the lower mounting facility about the cross origin when the upper and lower mounting facilities are positioned about a joint and the cross origin is positioned at a point relative to the joint and the point is on a side of the joint opposite a direction of the extension. In some embodiments, the point is one of: a location in an antecubital fossa of a wearer's elbow; a location in a popliteal fossa of a wearer's knee; a location proximal to a talus bone of a wearer's ankle; a location proximal to a lumbar area of a wearer's back; or a location in the axillary fossa of a user's shoulder.

Some embodiments of the methods of use provide a method of supporting a wearer's joint, the method comprising the steps of securing a first portion of an elastic cross strap about one body portion joined to a second body portion at a wearer's joint, positioning the elastic cross strap about the joint to form a cross origin at a point of the joint and securing a second portion of the elastic cross strap about the second body portion at the joint whereby the elastic cross strap is capable of providing resistance to an extension of the wearer's body portions about the joint.

In some embodiments of the methods of use, the joint may be one of: an elbow; a knee; a shoulder; a back; or an ankle.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawing depict only typical embodiments of the invention and are not therefore to be considered to be limiting of its scope, the invention will be described and explained with additional specificity and detail through the use of the accompanying drawings in which:

FIG. 17C illustrates an anterior view of an example embodiment of a brace for a wearer's knee;

FIG. 17D illustrates a posterior view of an example embodiment of a brace for a wearer's knee;

DETAILED DESCRIPTION OF THE INVENTION

Although example embodiments are described in detail for use with knee bracing and reinforcement, it is understood that the methods and systems described can be used for similar medical situations where support of and resistance to moving joints may be needed. Examples of embodiments with other joints such as but not limited to the shoulder, elbow, back and ankle are also described and illustrated below. Notwithstanding the specific example embodiments set forth below, all such variations and modifications that would be envisioned by one of ordinary skill in the art are intended to fall within the scope of this disclosure.

Some embodiments of this elastic brace assembly comprise a non-rigid or semi-rigid brace utilizing an elastic cross strap to provide a progressive resisting force to joint movement such as hyperextension. Some embodiments of this brace assembly may include a flexible sleeve or other traditional brace components. Although some embodiments of the assembly do not need side hinges, metal upright stays or braces and hinges, it is contemplated that some embodiments of the brace assembly may also include these elements.

One Embodiment of the Brace Assembly:

Although it is contemplated that embodiments of the assembly can support many different types of skeletal joints such as elbows, ankle, shoulder, backs, wrists or knees, the illustrative examples below will use an embodiment directed to support a person's knee. Therefore, references to anatomical portions of the wearer's knee are for illustration purposes and not as a limitation.

Example embodiments of this new brace assembly comprise at least one elastic hyperextension cross strap, at least one upper mounting facility and at least one lower mounting facility. In these embodiment, generally, the upper mounting facility positions and secures the brace assembly about the thigh area of a user's leg, the lower mounting facility positions and secures the brace assembly about the shin area of the user's leg and the elastic hyperextension cross strap attaches to the upper and lower mounting facilities whereby the elastic cross strap can provide progressively increasing resistance to the extension of the user's knee when the elastic cross strap is positioned posterior to the user's knee. In some embodiments, the upper and lower mounting facility are defined entirely by the elastic cross strap to help secure the assembly to the user's leg. In some embodiments, the upper and lower mounting facilities are separate elements defined by portions of brace elements, such as upper and lower cuffs/pads or side braces, cooperating with the elastic cross strap.

In some embodiments, the brace assembly stabilizes the knee from hyperextension in the 5-25 degree range.

Figure 1A:
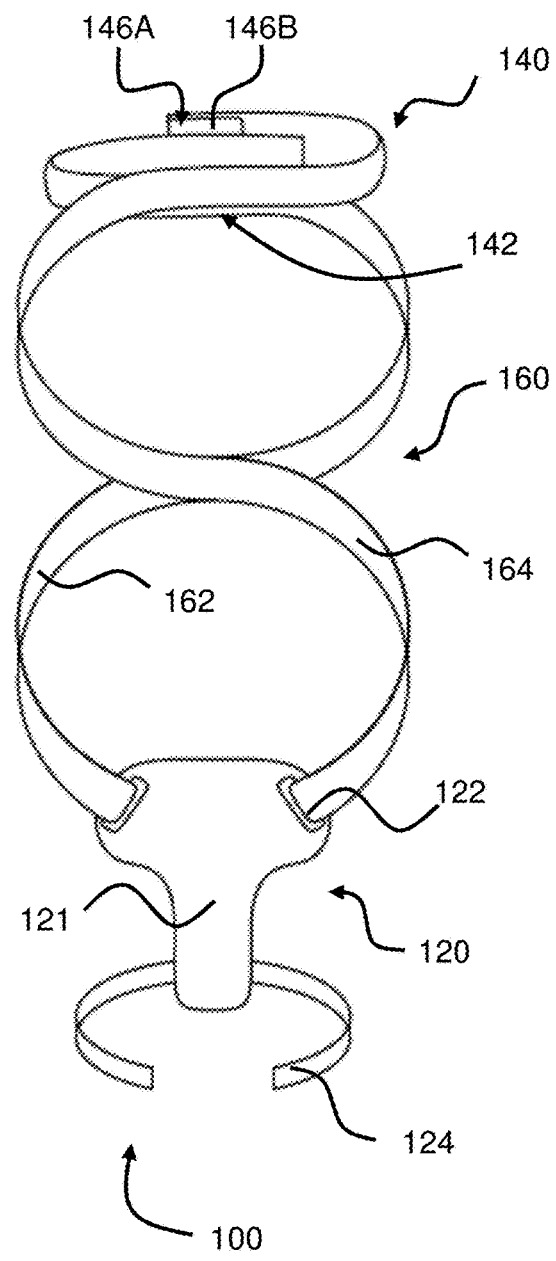
FIG. 1A illustrates a front view of one embodiment of the brace assembly showing a shin shell.
Figure 1B:
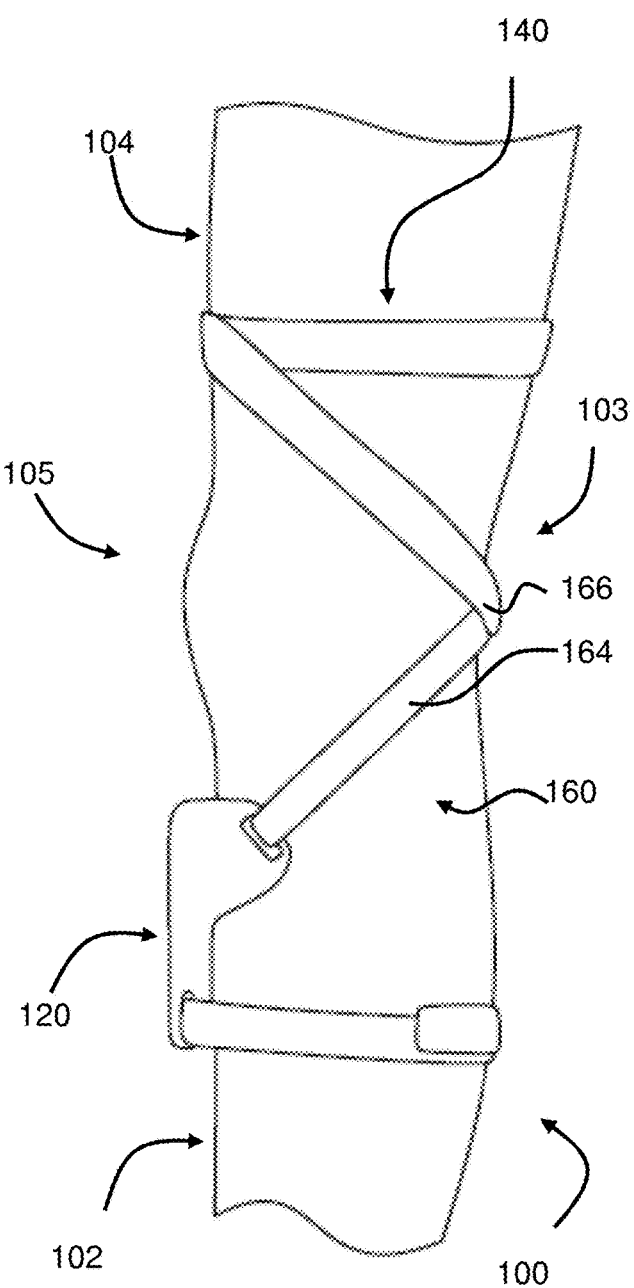
FIG. 1B illustrates a side view of the embodiment the brace assembly of FIG. 1A mounted on the knee of a wearer.

As shown in the example embodiments of FIGS. 1A and 1B, the elastic cross strap 160 is at least one elongated element able to provide a progressive tensile resistance force and capable of creating a cross pattern that creates a cross origin and cross strap arms. The elastic cross strap also comprises means to attach ends of the straps, the cross strap arms, to the upper and lower mounting facilities. In some embodiments, the elastic cross strap comprises the combination of multiple elongated elastic straps, cross strap arms, that may be configured to create the cross pattern that creates the cross origin and cross strap arms. In some embodiments, the elastic cross strap comprises a single cross strap that may be configured to create the cross pattern that creates the cross origin and cross strap arms. In some embodiments, the elastic cross strap comprises a single cross strap that has cross strap arms coming from a pre-defined or integrated cross origin.

In some embodiments, the elastic cross strap comprises one or more straps of pre-determined lengths and elastic cross straps are selected based on the length needed for that wearer. In other embodiments, the elastic cross strap has adjustment elements that allow the cross strap to be adjusted to fit the wearer and provide different resistance properties to help prevent joint extension.

The elastic cross strap can be made from material to provide resistance to stretching in one direction. In one example embodiment, the elastic cross strap is a pliable elastic material that provides progressive resistance to stretching and as the material stretches, the resistance to stretching increases. As an example, the resistance properties of embodiments function similar to the resistance properties of a rubber band. In one embodiment, the elastic material is similar to elastic sports tape. In other embodiments, the elastic material can comprise a rubber material, a plastic material or a spring that can provide resistance properties similar to those of a rubber band. It is also contemplated that the elastic cross strap may comprise a combination of elastic and non-elastic material that still provide the elastic properties required of the strap. As an example, and not for limitation purposes, these combinations may comprise combinations or laminates including cloths, fabrics, threads, struts or other materials combined with an elastic material through sewing, adhesives, Velcro® type attachment or even simple adjacent placement to elastic materials. These combinations or laminates may comprise multiple materials that can increase the adherence of the cross strap to itself or other materials and may be comprise combined materials at particular, not all areas of the cross strap. Combinations of elastomeric materials with varying resistance properties are also contemplated.

The length, width and elastic properties of the elastic cross strap can be varied based on the properties desired for the wearer and/or the sport the wearer will participate in. Although some of the discussion relates to a single elastic cross strap, it is understood that multiple elastic cross straps or straps can be used to provide the functional properties of the elastic cross strap. More than one elastic cross strap or strap can be used such that their properties combine to provide the desired resistance properties.

As shown in FIG. 1A, the elastic cross strap 160 has two cross strap arms 162 and 164 respectively configured to attach to a lower arm end to a lower mounting facility 120 at a lower attachment point. The lower mounting facility further comprises securing elements, such as straps 124 to engage the wearer's lower limb as well as points to attach this element to the other elements of the assembly. Embodiments of the lower mounting facility include but are not limited to a hard shell, pad, cuff, portions of the strap, portions of a sleeve or any other element capable of mounting the brace to the wearer's limb. In this embodiment, the lower mounting facility 120 is a shin shell 121 mounted anterior to the knee and just below the wearer's knee with one or more securing strap 124. In this embodiment, the tibial shell can be made of a flexible material or when desired, it can be made of more rigid material to provide some tibial protection to the wearer.

Means to attach or couple the elastic cross strap arms to the mounting facilities include, but are not limited to common attachment means such as: rigid fasteners such as rivets, adhesives or sewing; slidable attachment points such as slots or channels, pivoting fasteners such as rivets or buttons; and removable fasteners such as Velcro, buttons, buckles, snaps or hooks. It is contemplated that the means of attachment, such as with Velcro straps or buckles, will let the cross strap be tightened or loosened as desired for comfort, support or specific resistance reasons.

As shown, the attachment of the elastic cross strap in FIG. 1 is through lower attachment points that comprise multiple openings 122 in the shell positioned so that the elastic cross strap arms 162 and 164 weave through the shell and extend up towards the wearer's thigh. When installed as in FIG. 1B, these elastic straps extend from the anterior tibia at the patellar attachment and wrap posterior with one wrapping medial and one wrap laterally to attach to the wearer's anterior thigh pad. This "X-strap" configuration creates elastic straps running from an anterior tibial pad 121 with one strap medial and one strap lateral to cross like an X in the popliteal fossa 103 behind the knee 105, then coming back to an anterior of thigh pad 140 in the middle to upper one-third of the thigh.

It is also contemplated that the shin shell can be configured to allow the same straps, or additional straps, clips or bands, to wrap around the wearer's lower leg to secure the lower arms of the elastic cross strap.

The upper mounting facility positions the brace assembly about the upper limb of a wearer's joint. Embodiments of this facility can similarly include those possible for the lower mounting facility. In the embodiment shown in FIG. 1, the upper arms of the elastic cross strap are configured to connect to each other and perform the function of the upper mounting facility 140, much like a thigh pad in a traditional knee brace. In this embodiment, the thigh side connection is made by connectors 146A and 146 B on the end of the upper arms extending up the wearer's thigh. As shown, this connection is made by complementary hook and loop type Velcro fasteners on the thigh end of the straps but any connection or coupling means can be used such as but not limited to complementary hooks, buttons, buckles, slots, loops, adhesives or clips. In this embodiment, the thigh end of the straps can provide the functionality of a thigh cuff in traditional knee braces by wrapping the straps around the wearer's thigh to help secure the assembly to the thigh. In the embodiment shown, sections of the upper arms also contain optional facility attachment elements defining a facility attachment point 142 that allows the upper arms to attach to the upper mounting facility in particular places such as the anterior position shown. Examples of attachment element can include all those possible for the lower mounting facility. In one embodiment, the attachment elements comprise matching Velcro sections attached on the upper arms of the elastic cross strap. These sections are placed on the elastic cross strap arms 162 and 164 in pre-determined locations that will allow proper positioning of the elements and help ensure the attachment can be maintained anterior to the limb and towards a front portion of the mounting facility.

For the embodiment of FIG. 1, the attachment point 142 functions generally as an upper anterior resistance point and a point generally mid-way between the lower attachment points functions as the lower anterior resistance point.

Figure 2:
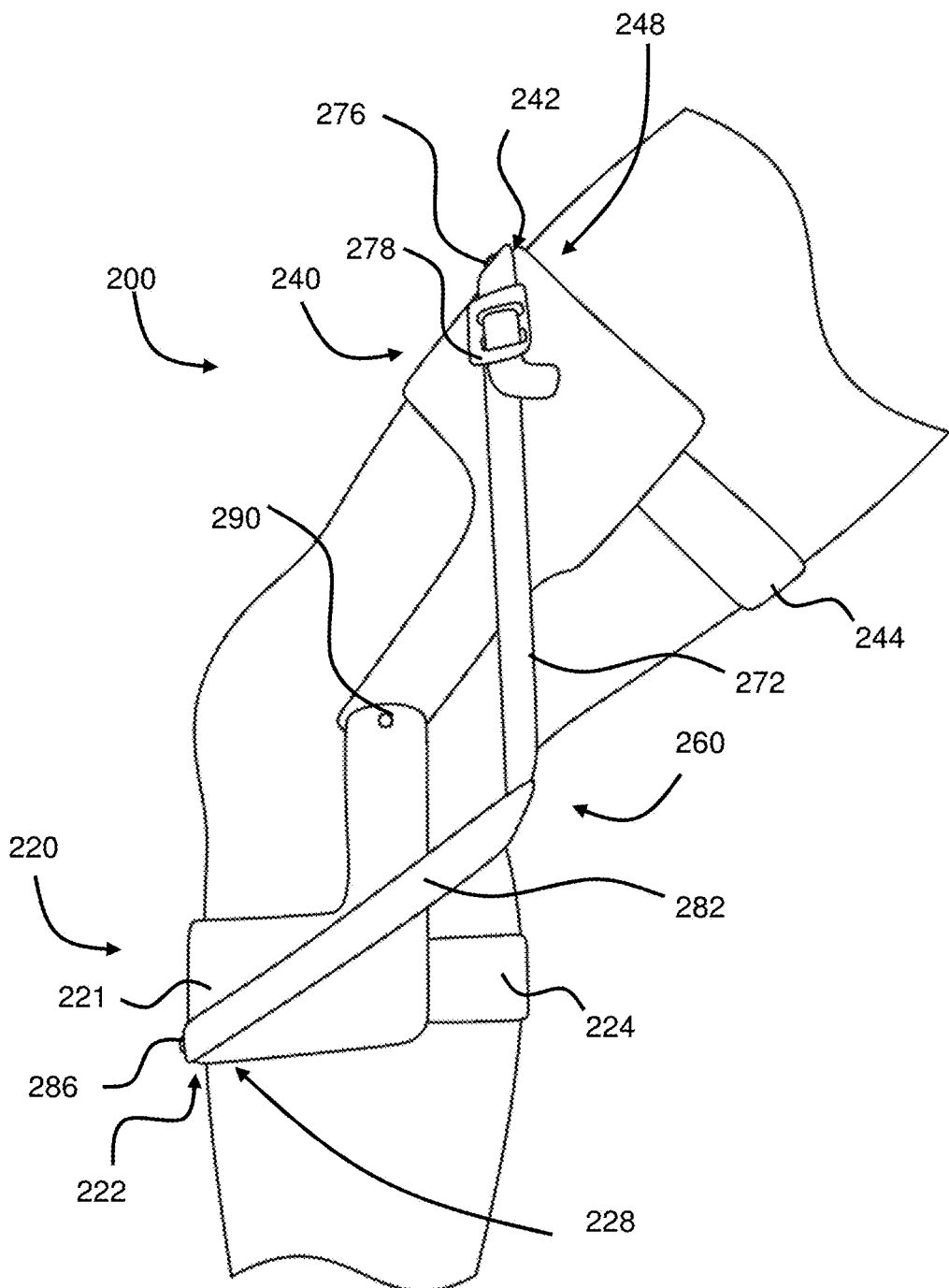
FIG. 2 illustrates a side view of one embodiment of the brace assembly having an upper and lower mounting facility.

In embodiments where the upper mounting facility comprises an upper pad or thigh pad, as shown in FIG. 2, the thigh pad 240 can comprise any non-rigid material that can engage the wearer's thigh and attach this pad to other elements of the assembly. Suitable materials for this pad include but are not limited to cloth, cotton, plastic, nylon, mesh, leather and elastic materials. This pad may further include padding or may be heat pliable, molded or contoured to be more comfortable for the wearer. The embodiment in FIG. 2 illustrates one embodiment of an anterior thigh pad 240 which can be shaped to the contour of the medial anterior thigh above the vastus medialis oblique.

FIG. 2 also shows that embodiments of the assembly 200 can include a lower mounting facility 220 having a tibial pad 221 with similar mechanical characteristics as the thigh pad 240.

In embodiments, as shown in FIG. 2, the mounting facilities 220 and 240 include at least one securing strap, here lower and upper securing straps 224 and 244, operably connected to the facilities to secure them onto the wearer's limbs. Any means to secure the pads and tighten the pads onto the wearer's body is suitable. In one embodiment, a Velcro type securing strap is attached to each of the pads and when the strap is secured to the pad around the wearer's limb, the pads are secured to the wearer. Other suitable means to secure the facilities to wearer's limbs include but are not limited to a sleeve around the limb and straps with adjusting facilities such as buckles.

It is contemplated that in some embodiments, rather than connecting or coupling the elastic cross strap 260 to the pads, the securing straps 224 and 244 can also provide the attachment means for the pads to the elastic straps. For example, the securing strap may wrap all the way around the limb and have the attachment means so that when the securing strap is secured to the pads, the elastic cross straps are attached to the securing strap.

The elastic cross strap 260 is attached to the upper and lower mounting facilities at upper and lower facility attachment points 242 and 222. This attachment can be made using any means that will secure the ends of the elastic cross straps onto the mounting facilities and is generally made at a front portion of the mounting facility. As shown in FIG. 2, the elastic cross strap arms are permanently attached to the attachment points 242 and 222 on the facility front portions 248 and 228 by rivets at strap attachment points 276 and 286. Attachment means includes any of the attachment means already described. If the thigh pad is not used, the elastic cross straps can be wrapped around the wearer's thigh and connected to themselves to secure the assembly to the wearer.

For the embodiment of FIG. 2, the attachment points 242 and 222 function generally as the upper and lower anterior resistance points respectively.

FIG. 2 also illustrates the adjusting facilities that can be used to adjust the length of the elastic cross strap. By adjusting the length of the elastic cross strap, the elastic tension and resistive properties of the cross strap can be adjusted. Adjustment element 278 comprises a buckle that allows the arms 272 and 282 of the elastic cross strap to be put through the buckle and adjusted. (An adjusting facility on the other side of the brace can be provided but is not shown.) Examples of suitable adjusting facilities include but are not limited to buttons, Velcro, snaps or hooks or any type of adjustable connections that allows a connection that can alter the length or resistance properties of the elastic cross strap. It is understood that providing elastic cross straps of varying length is also another example of a suitable adjusting facility.

FIGS. 1B and 2 illustrate the extension of the brace and the limbs about the joint. FIG. 2 illustrates one example embodiment of a brace and knee where the brace and knee joint are slightly bent. FIG. 1B illustrates one example embodiment of a brace and a knee joint extended from a position such as in FIG. 2. An extension of the brace or the limbs about the joint, when used herein as a verb, is the action by which the brace or the limbs about the joint are extended from a bent position to a straight position (180° angle) or sometimes beyond a straight angle (e.g. hyperextension).

Figures 3A, 3B:
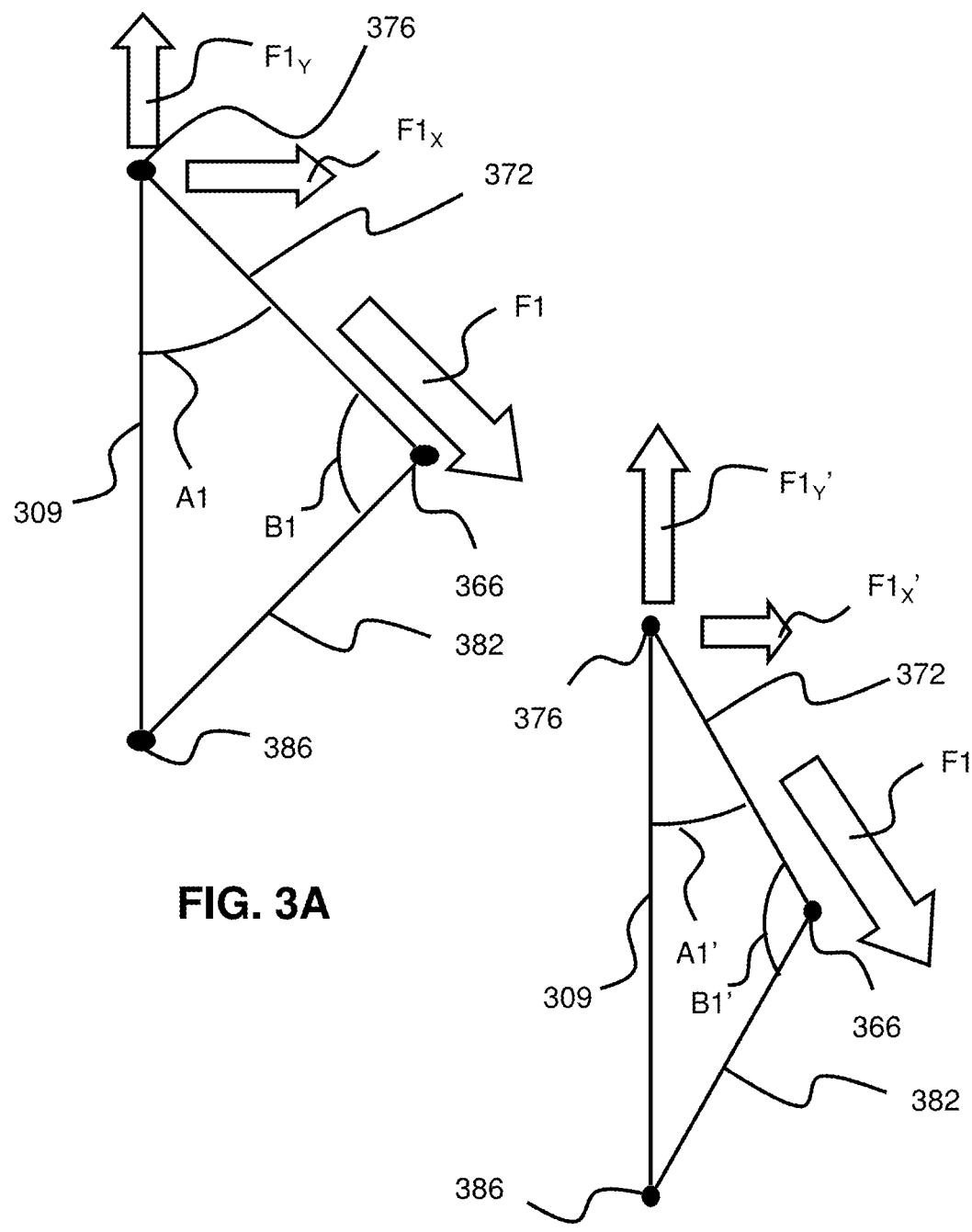
FIG. 3A illustrates the force patterns of one embodiment of the cross strap when mounted around a knee.
FIG. 3B illustrates the force patterns of one embodiment of the cross strap when mounted around a knee.

In some embodiments of this brace assembly, it is beneficial for the elastic cross strap to provide a sufficient resistance force to an extension of the limbs about a joint at or near an anterior point of the wearer's leg. This resistance force is applied to the limbs about a joint by resisting an extension of elements of the brace itself between the cross origin and the anterior resistance points. By resisting the extension of elements of the brace, such as the anterior resistance points about the cross origin, elements of the brace are able to help limbs resist their extension about the bending axis of the joint. The bending axis of the joint is the actual or conceptually equivalent point of the joint about which the limb/body portions bend or rotate. When the cross origin is positioned posterior to the joint, which is posterior to the joint's bending axis such as in a fossa of the joint, this typically means that the anterior resistance point may be positioned anterior to the joint at a front portion of the mounting facilities. The anterior resistance point is typically the point at which the resistance force is applied to the brace portion that applies that resistance force to an extension force applied to the brace by the extension of the limbs. In most, but not necessarily all embodiments, the anterior resistance point is the same as the attachment points. For example, as represented in FIGS. 3A and 3B, this assembly benefits from a configuration that maximizes the tensile force that the elastic cross straps can provide. In FIG. 3A, the lines 372 and 382 represent the upper and lower elastic cross strap arms respectively of an elastic cross strap and the points 376 and 386 represent their strap attachment points and point 366 represents the cross origin. In the embodiment illustrated, the cross origin 366 would be posterior to the joint bending axis. The attachment points represent examples of the upper and lower anterior resistance points from which the cross strap provides the resistive force that counters the extension force caused by a joint extending. The line 309 generally represents the front part of the wearer's leg. Using the upper strap attachment point 376 as an example, the resistance force F1 that upper elastic cross strap upper arm 372 provides at the upper anterior resistance point can be translated into F1subX and F1subY forces as shown. Using trigonometric and static principals, the angle A1 allows the force to be translated in the X direction as F1subX=F1 (sin A1). As compared to FIG. 3B, where the angle A1 prime of the elastic cross strap arm 372 to 309 is less than A1, the resistance force F1subX to be applied is less. Therefore, as designed, the attachment of the elastic cross strap onto the brace assembly towards the anterior, or front portion of the brace, provides more resistance than known prior art brace assemblies with straps that provide predominantly posterior resistance points and smaller angles at A1. This positioning also reduces the force that would otherwise be put on the brace in the direction of F1subY. By reducing this force, the forces that would tend to cause the brace mounting facilities to migrate towards each other are reduced.

The resulting angles shown in FIGS. 3A and 3B will vary for each patient given their size, strength in order to control extension of the joint. In some embodiments of the brace assembly, the angle from the lower attachment point and upper attachment point about the cross origin (FIG. 3A angle B1) can be in a range of about 50 to 160 degrees, 60 to 140 degrees or 75 to 115 degrees.

In addition to providing superior resistance properties, embodiments utilizing an elastic cross strap may also provide the benefit of eliminating the immediate hard stop typical of prior art embodiments that use hard stop features such as in a hinge or with a non-elastic strap. This lack of a hard stop helps prevent migration of the brace and reduces the jerking feeling making the brace more comfortable for the wearer. The inclusion of providing progressive resistance with the elastic cross strap provides additional benefits. The elastic properties of the cross strap can provide resistive properties earlier in the motion arch of the joint thereby controlling extension sooner. Additionally, the elastic properties can provide increasing resistance in a linear fashion as the joint goes from flexion to extension which increases neuromuscular control and causes the extensor muscles to gradually strengthen which is good for joint stability.

In some embodiments, the elastic cross strap has a limiting resistance capability. For these embodiments, the limiting resistance may be provided by the elastic properties of the elastic cross strap reaching its maximum extension and therefore the cross strap provides a direct resisting force to further cross strap extension. This limiting resistance may also be provided by having a non-elastic material used in combination with an elastic material whereby when the limiting resistance point is met, the non-elastic material is engaged and that provides the direct resisting force to any further extension of the elastic cross strap.

Figures 4A, 4B:
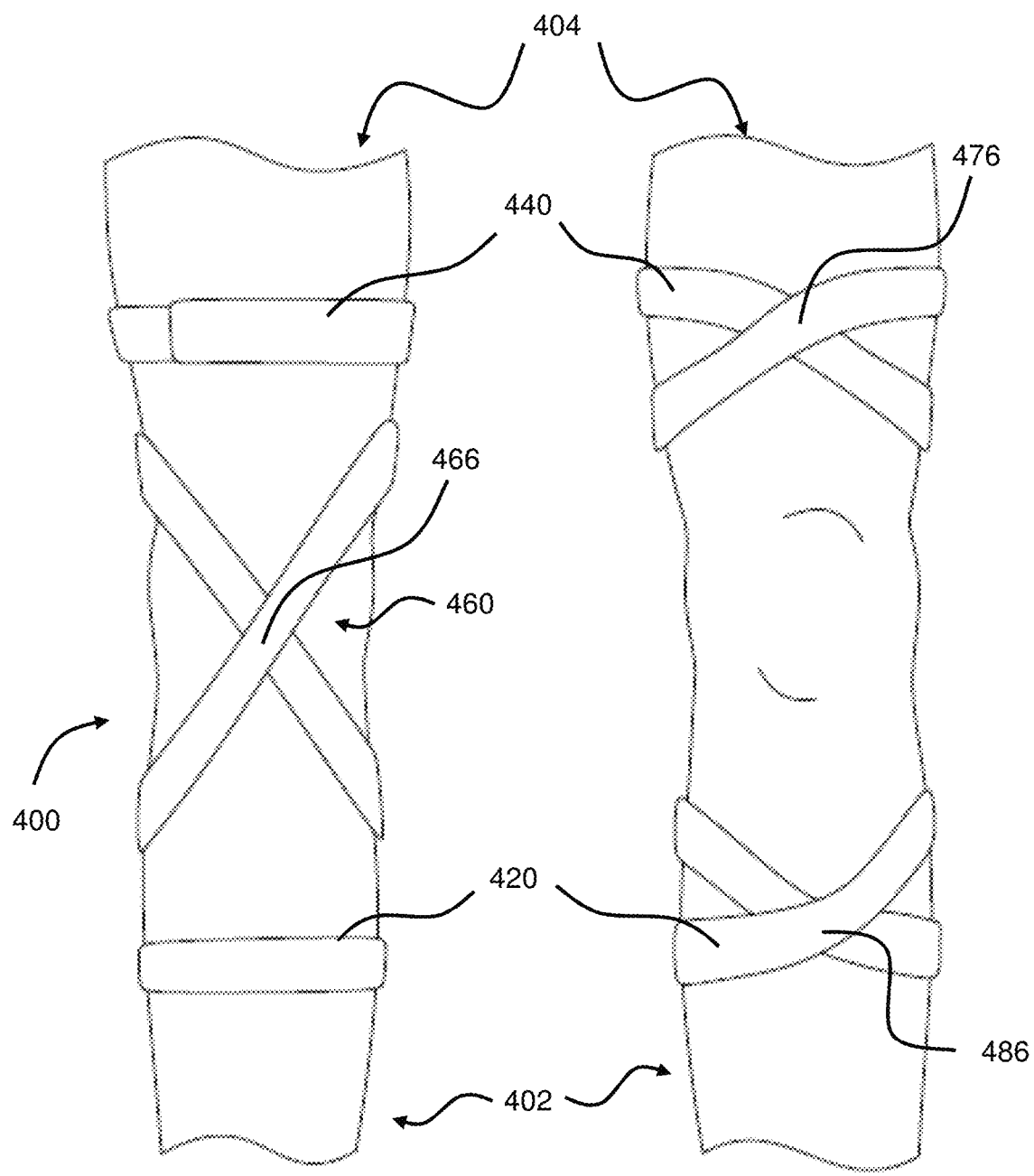
FIG. 4A illustrates a front view of one embodiment of the brace assembly comprising a single cross strap about the knee of a wearer.
FIG. 4B illustrates a rear view of one embodiment of the brace assembly comprising a single cross strap about the knee of a wearer.

Other Embodiments of the Brace:

One embodiment of the brace assembly comprises a single elastic cross strap mounted in a way that provides the functionality of the brace. As shown in FIGS. 4A and 4B, this embodiment comprises a single elastic cross strap 460 that is wrapped around the wearer's shin 402 to create the lower mounting facility 420, the arms of the elastic cross strap are then wrapped behind the knee to cross in the popliteal fossa of the knee to create the cross origin 466. The arms are then extended and wrapped around the wearer's thigh 404 to create the upper mounting facility 440.

In this embodiment of the brace assembly 400, the wrapping around the shin 402 may start with the middle of the elastic cross strap 460 being placed in the back of the calf. The wrapping can continue around the lower leg once or multiple times. At the point that the elastic cross strap is extended from a position anterior to the shin and then up behind the knee. There may be elements to help define the strap attachment points 486 to assist in keeping the arms of the cross strap properly positioned anterior to the joint. The wrapping around the thigh 404 may also be done once or multiple times with attachment means or coupling means such as hooks, bands, buttons, buckles, loops, clips, Velcro or straps to keep the straps together and define the strap attachment point 476. To close the elastic cross strap, any connection means already disclosed, such as complementary hook-and-loop (Velcro) connectors can be used to secure the upper arms to each other. For the embodiment illustrated in FIGS. 4A and 4B, the strap attachment points 476 and 486 function generally as the upper and lower anterior resistance points respectively.

Although the embodiment in FIGS. 4A and 4B illustrate an embodiment of a single strap with two free ends, embodiments of one single strap in a loop are contemplated that can similarly be used as the brace assembly.

Figure 10:
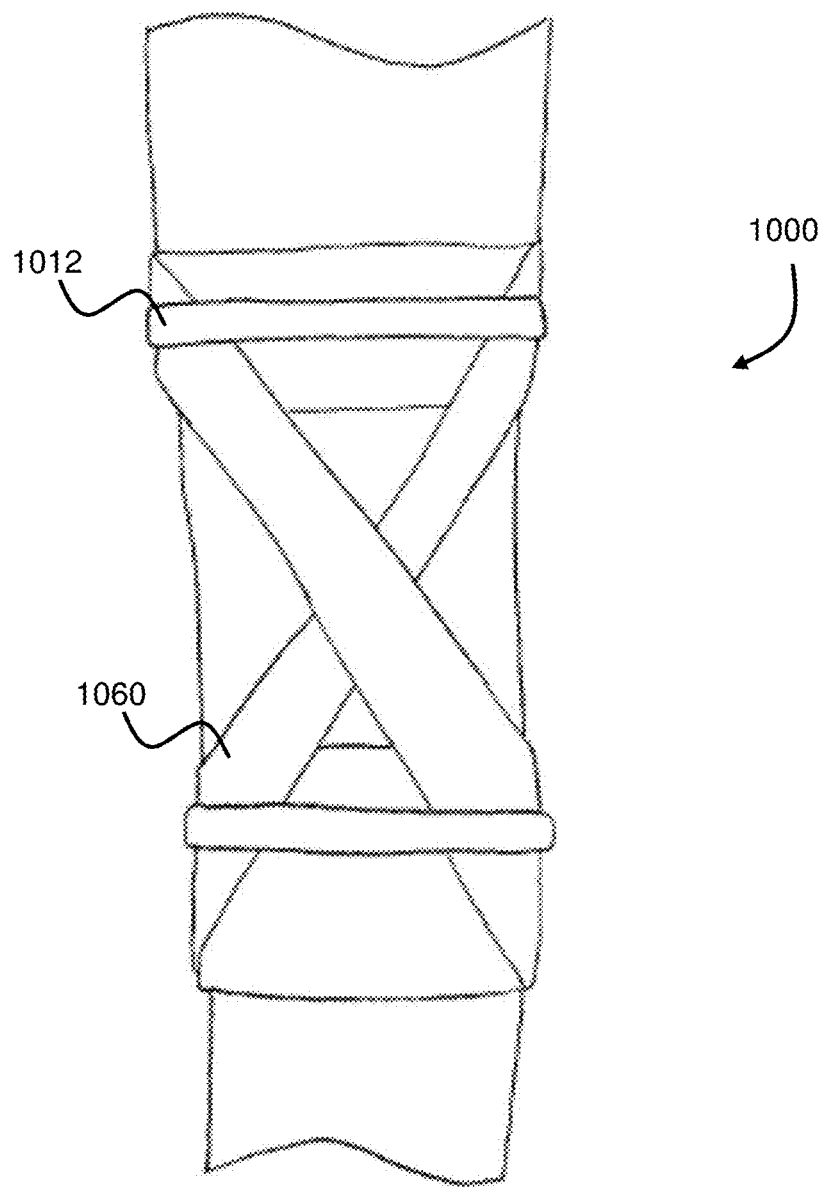
FIG. 10 illustrates a rear view of another embodiment of the brace assembly.

One embodiment similar to that in FIGS. 4A and 4B is shown in FIG. 10. This embodiment comprises an elastic wrap material such as latex or latex-free Esmark Wrap sold by Medline Industries of Mansfield Mass. being used as the cross strap. The elastic wrap 1060 is positioned about the joint as described with the embodiment shown in FIGS. 4A and B and secured about the wearer's leg by any type of securing means such as an adhesive tape 1012, securing the elastic wrap to itself by wrapping it around the leg in multiple layers or by having a multiple property elastic cross strap that allows the strap to adhere to itself.

Figure 5:
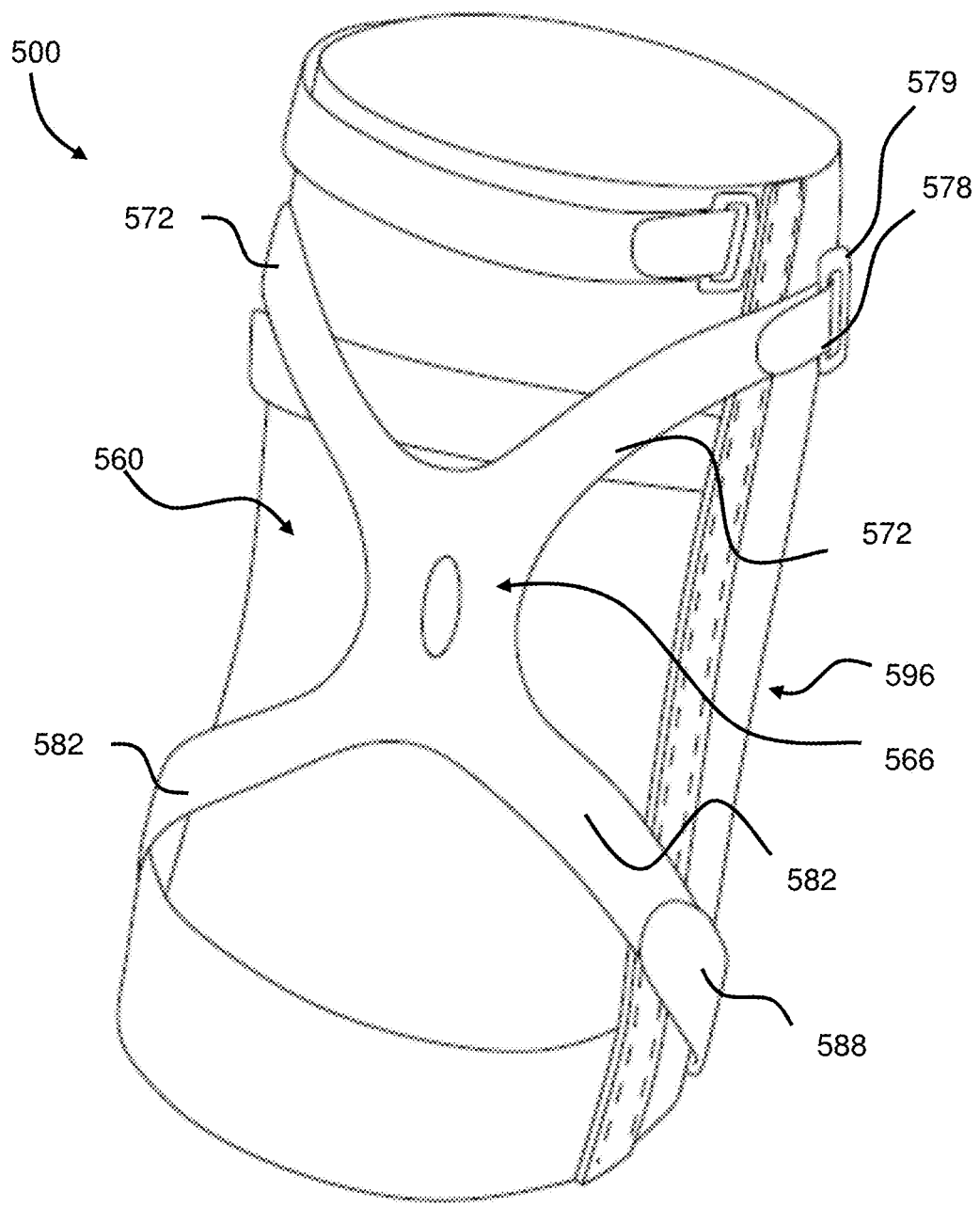
FIG. 5 illustrates a rear view of one embodiment of the brace assembly having an x-shaped cross strap cooperating with a sleeve.

Another embodiment of the brace assembly utilizes a single elastic x-strap as the elastic cross strap. As shown in FIG. 5, the assembly 500 has a single elastic cross strap 560 having a cross origin 566, upper arms 572, lower arms 582 and attachment points (shown in FIG. 6 as fasteners 673 and 683). This elastic cross strap functions similar to the crossed single elastic cross strap. As shown, the elastic cross strap arms have Velcro fasteners that act as adjustment elements 578 and 588 on their end. These ends connect through loops 579 that are attached to Velcro fasteners (not shown) on both the upper and lower mounting facility. Adjustment element 578 is able to be pulled through the loops 579 and secured to itself at different positions creating arms of different lengths. In one embodiment, this elastic x-strap is long enough to extend from the anterior tibia at the patellar attachment and wrap posteriorly with one arm wrapping medial and one wrapping laterally to attach to the wearer's anterior thigh pad. This elastic "X-strap" configuration creates arms running from an anterior tibial pad with one strap medial and one strap lateral to cross like an X in the popliteal fossa of the knee, then coming back to an anterior thigh pad in the middle to upper one-third of the thigh.

Similarly, embodiments having two elastic straps can be made where two elastic straps are used to create the elastic cross strap.

Figure 6:
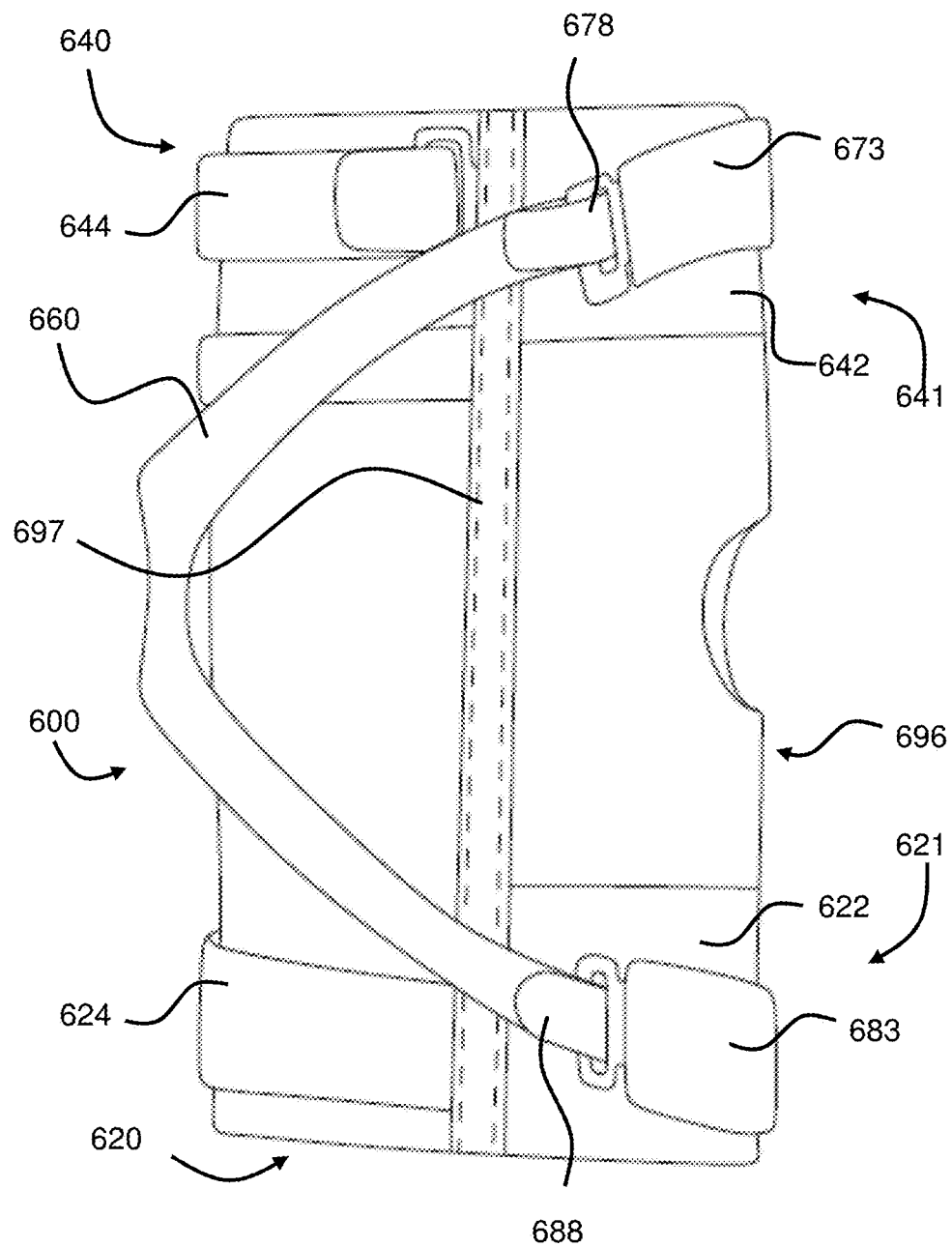
FIG. 6 illustrates a side view of one embodiment of the brace assembly showing the cross strap attachment to the upper and lower mounting facilities on a sleeve.

Embodiments of a brace assembly also include having a brace sleeve to provide assembly elements. This type of embodiment is shown in FIGS. 5 and 6. In FIG. 6, the upper and lower portions of the sleeve 696, portion 640 and 620, can function as the including the upper and lower mounting facilities respectively. The upper mounting facility 640 may comprise a portion as the upper pad/cuff 641 with an upper strap 644 helping secure the upper mounting facility 640 and cuff 641 to the leg. The lower mounting facility 620 may comprise a portion as the lower pad/cuff 621 with a lower strap 624 helping secure the lower mounting facility 620 and cuff 621 to the leg. The sleeve in these embodiments will rest against the wearer's skin and may be made of an elastic material. The surface of the sleeve that will touch the wearer's skin, the under sleeve, is a non-slick surface to frictionally engage the wearers limb. In the embodiment of FIG. 6, the inner surface of the sleeve 696 comprises an open faced diamond shaped web weave that frictionally engages the skin and also allows portions of the skin surface to be exposed. Other embodiments of the frictional surface of the under sleeve include but are not limited to high friction surfaces such as rubber, felt, mesh, elastic material or any combination of these surfaces. It is contemplated that under sleeve material can be used so that the under sleeve is in contact with the skin around the knee under the elastic straps to help keep them in place.

As shown in FIG. 6, embodiments of the brace assembly 600 can include additional fasteners 673 and 683. These fasteners provide the attachment between the upper and lower mounting facilities and the ends of the elastic cross strap 660 and function as the strap attachment points. With this configuration, the facility attachment points 642 and 622 on the mounting facilities comprises an entire anterior area of the brace having hook-and-loop type fasteners that can match with the under surface of the fasteners 673 and 683. In this configuration, the placement of the fasteners 673 and 683 up and down length of the brace adjusts the effective length of the elastic cross strap about the wearer's knee. This adjustment can be used in cooperation with the adjustment from the adjustment elements 678 and 688 to adjust the length of the elastic cross strap. Although these additional fasteners can be a separate element from the elastic cross strap and the cross strap arms, they function as an extension of the elastic cross strap.

Some embodiments of the brace assembly without metallic or rigid elements able to comply with current sporting regulations, such as the FIFA rules.

The embodiment shown in FIG. 6 also includes optional flexible uprights 697 on one or both sides of the brace. An upright as used in this description is a hinge that has a high degree of axial stiffness and a high degree of bending flexibility. Examples of suitable uprights would be coiled spring cables, chain links or ball-and-socket links, planar struts or flexible struts that prevent the upper and lower mounting facilities from urging towards each other when the assembly is subjected to the forces of the elastic straps. The upright has the capability to bend in one or more planes while not compressing. The upright can be directly connected to the pads, sewn into the sleeve or be attached to other elements that are connected to the pads to keep the pads from urging towards each other. In these embodiments, suitable material for the uprights include, but is not limited to metals, Kevlar or carbon fiber type construction that will provide flexibility but not let the upright compress. Suitable overall shapes for the upright include but are not limited to a flexible rod that easily allows flexing of the knee when the uprights are installed on the wearer's leg.

Embodiments of the brace assembly can also include traditional knee braces elements such as upper and lower frames with central hinges as well as structures for patellar control. The elastic cross strap could be added to these assemblies to provide additional support and hyperextension protection. As shown in FIG. 2, the elastic cross strap 260 can function with a thigh cuff 240 and a tibia cuff 221. The elastic cross strap crosses behind the knee and the arms attach to the facility attachment points 242 and 222 on the cuffs. The hinge 290 of the brace can be of any type uses with traditional braces to include, but not limited to monocentric hinges, polycentric hinges, flexible uprights or any other hinge commonly used in joint braces.

Embodiments of the brace assembly can also include an elastic cross strap with a single rigid side strut and hinge or flexible upright. For example, this type of embodiment could be worn as a prophylactic brace on the lateral side of the knee to reduce knee injuries and reduce the chances of rigid brace elements colliding with each other and interfering with the user's leg movement. In these embodiments, the cross strap can comprise any of the descriptions included herein and is attached to the side strut or upright using the attachments means disclosed. The single rigid side strut and hinge can be similar to any of the side brace and hinge designs disclosed and the flexible upright can be similar to any of the flexible uprights disclosed in other embodiments with or without a sleeve.

Figure 7:
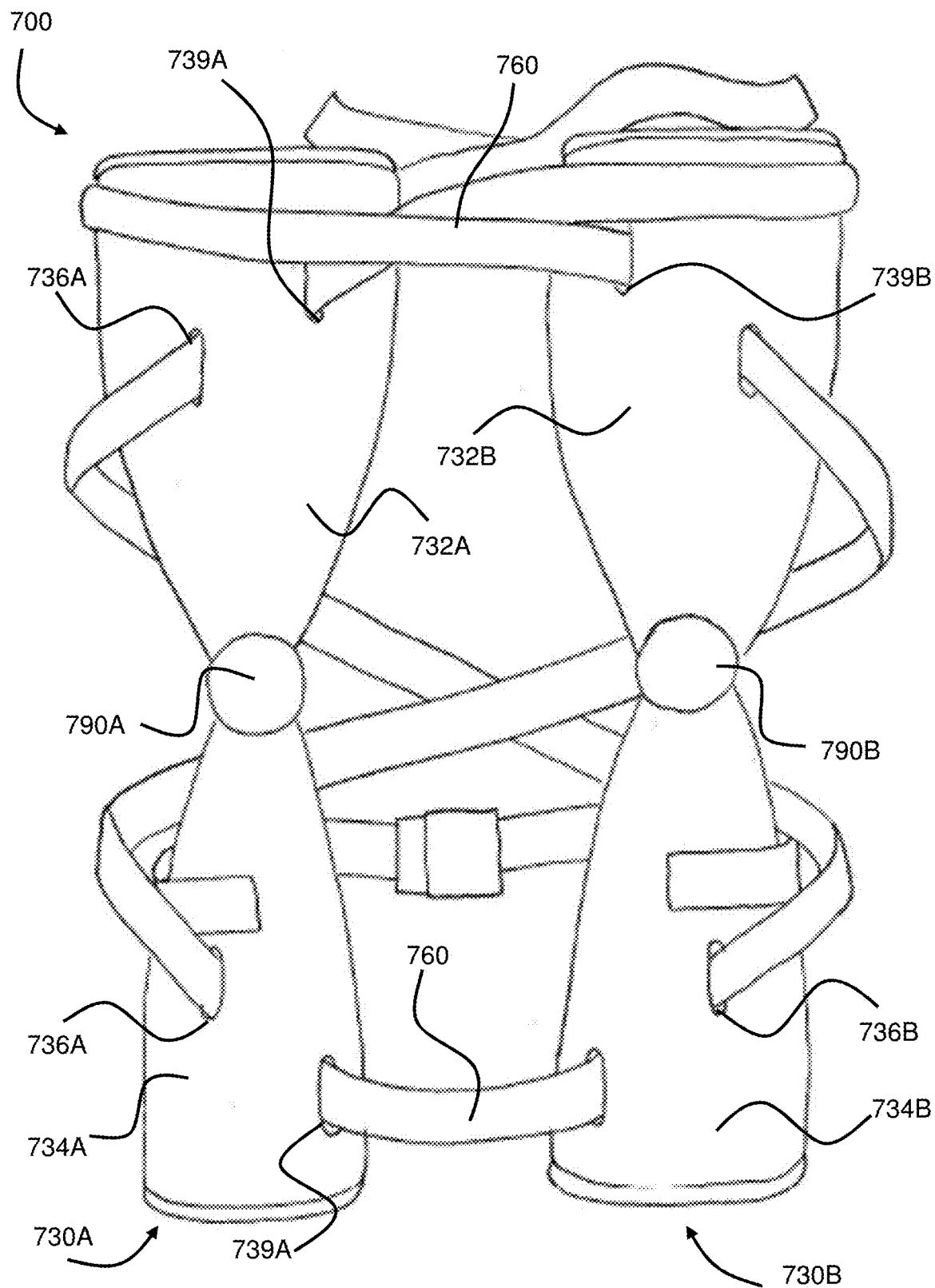
FIG. 7 illustrates a front view of another embodiment of the brace assembly with the side brace elements extended.
Figure 8:
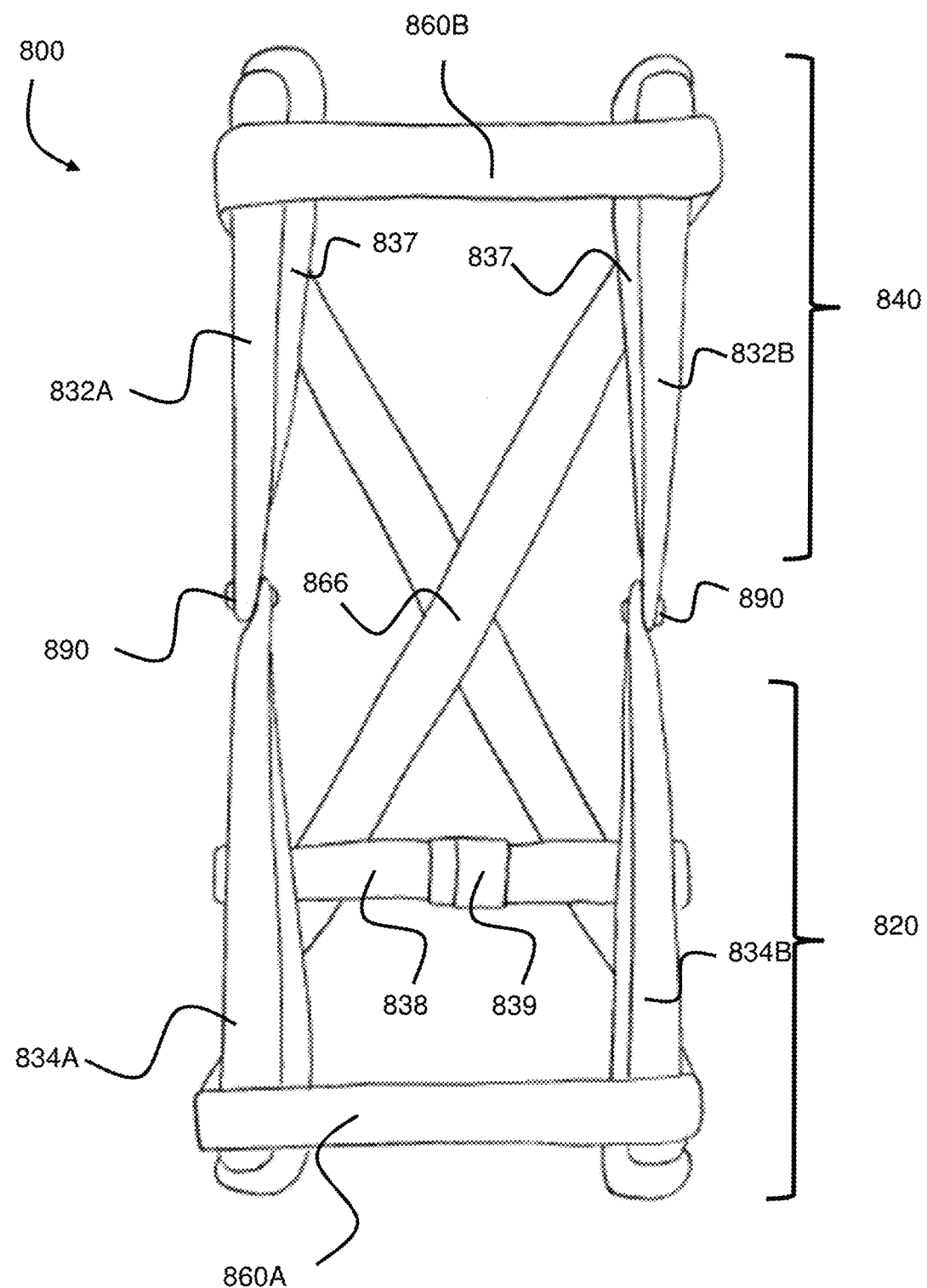
FIG. 8 illustrates a front view of one embodiment of a brace assembly positioned as if it were put on a wearer's leg.
Figure 9:
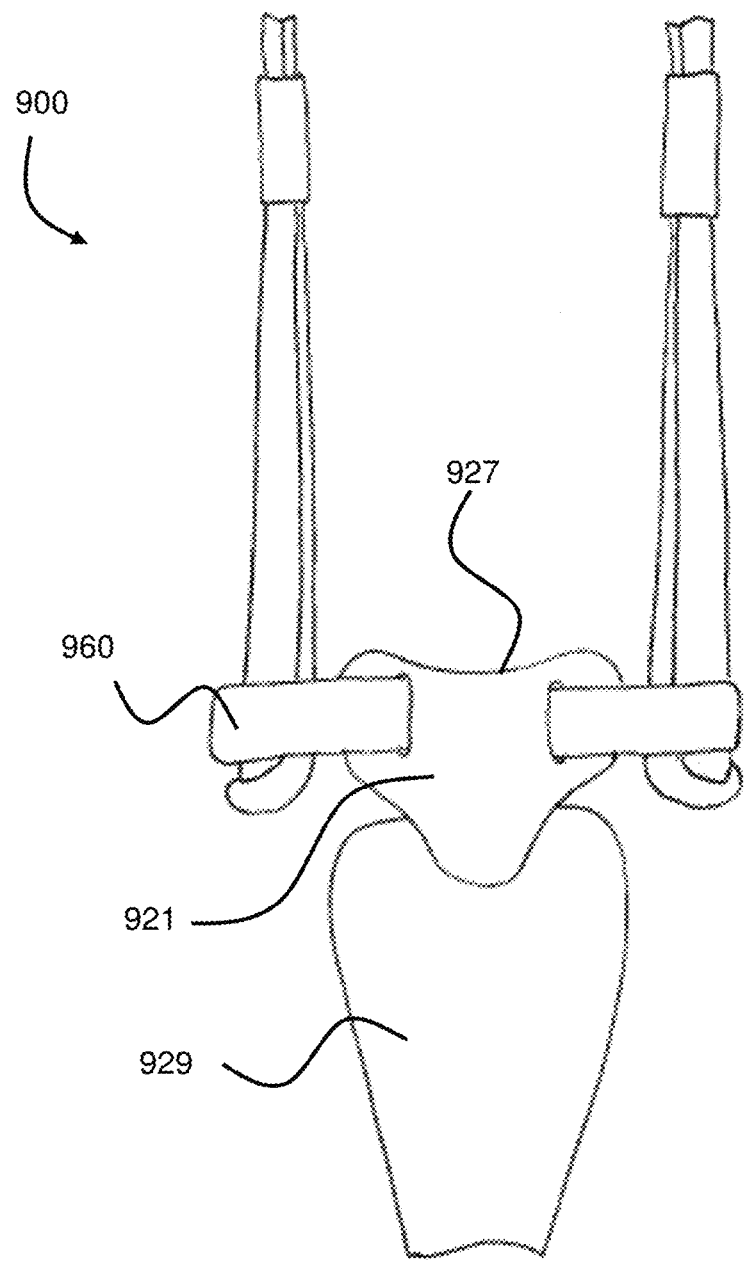
FIG. 9 illustrates a front view of another embodiment of the lower portions of a brace assembly with a shin shell positioned as if it were on a wearer's leg.

Additional embodiments of the brace assembly are shown in FIGS. 7, 8 and 9.

FIG. 7 shows a front view of one embodiment of the brace assembly 700 with the side brace elements 730A and 730B turned forward for illustration. In this embodiment, the upper and lower mounting facilities are defined by upper and lower portions of multiple side brace elements together with connector elements. One side brace element (e.g. medial) comprises an upper portion 732A, a lower portion 734A and a hinge 790A that allow the upper and lower portions to pivot relative to each other. Similarly, the other brace element (e.g. lateral) comprises an upper portion 732B, a hinge 790B and a lower portion 734B. This embodiment cooperates with an elastic cross strap 760 that is attached at various points to the side brace elements. As shown, the lower mounting facility is defined by the lower portion of both side brace elements (portions 734A and 734B) together with the portion of the elastic cross strap 760 attached to the lower brace portions. In a similar fashion, the upper mounting facility is defined by the upper portions (732A and 732B) of the medial and lateral brace elements cooperating with portions of the attached elastic cross strap 760.

The composition of the side brace elements in this embodiment can be of any rigid or semi-rigid material that can engage the side of a wearer's leg, attach the side elements to the elastic cross strap and provide a degree of rigidity to the assembly when stationary or when the upper and lower mounting facilities pivot about the hinges. Suitable materials include but are not limited to plastics, metals, composites or any combination of these materials. The brace elements may further include padding or may be heat pliable, molded or contoured to be more comfortable for the wearer. As shown (FIG. 8, 837), the side brace element includes an interior pad portion such as but not limited to foam, rubber, cloth, cotton, plastic, leather or any combination of these materials. The pad portion provides a comfortable surface between the more rigid side element portions and the wearer's skin. Side attachment points and on the side brace elements can include any means of attaching the elastic cross strap to the brace elements. As shown, one embodiment of the side attachment means comprises a series of slots such as 736A and 736B in the side brace elements. In this embodiment, the slots allow the elastic cross strap to be put into one slot such as 736A and exit another slot such as 739A. This "weaving" of the elastic cross strap through the side brace element attaches that portion of that elastic cross strap to that portion of the brace element. The side attachment points may allow the elastic cross strap and brace elements to be adjusted for each user. As shown, the weaving of the strap through the brace allows the strap to move within the slots and therefore adjust the position and/or tightening of the brace on a wearer. Although not required, in some embodiments, the attachment means are offset as shown with one means, typically the attachment means posterior to the joint, closer to the brace hinge and the other means, typically the means most anterior, furthest from the brace hinge. This configuration assists in the proper positioning of the cross strap within the brace and about the joint. Although weaving through slots are shown as an example attachment means in this embodiment, it is understood that any method of attaching the elastic cross strap to the side brace element is anticipated such as but not limited to hook-and-loop fasteners, hooks, buttons, clips, adhesives or any other attachment or connection means. When using the side brace elements, the side attachment points between the brace elements and the elastic cross strap do not always coincide exactly with the configurations of attachment points as described above and shown in FIGS. 1, 2, 4, 6 and in particular FIG. 3. It is understood that with side brace embodiments, the resistance to hyperextension can still be performed by the elastic cross strap that is wrapped around the front portion of the wearer's leg. In configurations that have attachment points about the side of side brace elements and the strap wraps around the limb, the elastic cross strap defines an anterior resistance point that will typically lie somewhere about half-way between the elastic cross straps attachment to one brace element and the other (for example, between 739A and 739B). It is from this anterior resistance point of the elastic cross strap, that the attachment point and anterior resistance point benefits described in FIGS. 3A and 3B are gained.

Figures 11A, 11B:
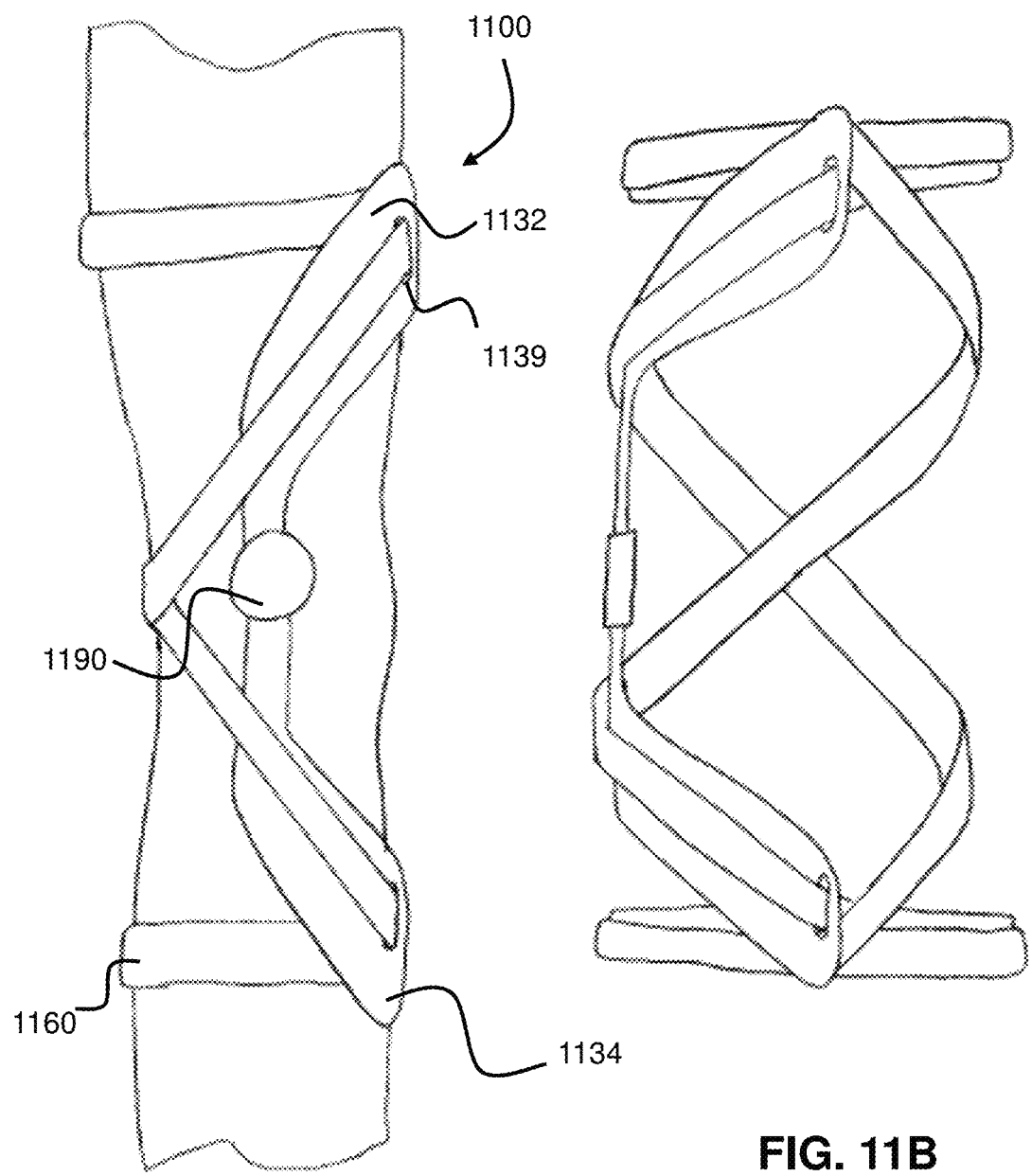
FIG. 11A illustrates a side view of another embodiment of the brace assembly mounted about a wearer's knee.
FIG. 11B illustrates a front view of the embodiment in FIG. 11A as if it were on a wearer's leg.

It is understood that alternative shapes of side braces may be used. For example, and not for limitation, one embodiment shown in FIGS. 11A and 11B comprises brace assembly 1100 having a single lateral side brace configured with upper and lower paddle shaped side brace elements 1132 and 1134 respectively, extending from the hinge 1190 and hooking towards the anterior side of the brace assembly. In this embodiment, the paddle shape provides some rigidity to the brace assembly while also helping the cross strap 1160 maintain a beneficial position anterior to the joint providing a better anterior resistance point. Additionally, because only one lateral side brace is used, this can minimize the collision of brace assembly elements that may otherwise occur with rigid or semi-rigid medial side brace elements. In this embodiment shown, the attachment means, such as slot 1139, can be positioned on the end of the paddle so that it will allow both the attachment of the cross strap coming from the lateral side of the joint, as well as help secure the cross strap coming from the medial side of the joint. As shown, the slot 1139 is positioned lower on the paddle end so that the cooperation of the paddle end and the cross strap coming lateral helps position the cross strap portion going medial from the upper mounting facility so that it is not urged towards the joint when put under tension. The same type of configuration can be used on the lower paddle as shown. It is understood, that other means to guide the cross strap at the ends of the paddles can be used such as but not limited to ridges, multiple slots, channels, rings or other attachment means. For example, in one embodiment, the distal ends of the paddles can have two open slots that are dimensioned to allow the cross strap to be easily put into the slots while the slots help prevent the cross strap portions in the slots from urging towards the joint when the strap is put under tension.

The composition of the elastic hyperextension cross strap is similar to the descriptions described for other embodiments. The composition, function and design of the elastic cross strap and other elastic components of the brace assembly may be similar to the elastic portions of the training brace assembly as described in U.S. patent application Ser. No. 13/541,796 filed Jul. 5, 2012 and published as U.S. Pub. No. 2012/02700708 on Oct. 25, 2012 which application is herein incorporated by reference in its entirety.

When assembled, as shown in FIG. 8 (with the wearer's knee), embodiments of the brace assembly function similar to the embodiments describe herein. The upper mounting facility is shown generally as 840 and the lower mounting facility is shown generally as 820. The upper portions (832A and 832B) and lower portions (834A and 834B) of the brace elements can pivot about the hinges 890. A portion of the elastic cross strap (860B) wraps around the front of the wearer's leg about the thigh, another portion of the elastic cross strap (860A) wraps around the front of the wearer's leg about the tibia and the elastic cross strap crosses behind the knee creating a cross-origin 866. The side brace elements help keep the position of the elastic cross strap as well as provide some rigidity to the assembly.

Shown in FIGS. 7 and 8, an optional securing strap 838 can be strapped around the wearer's leg to help secure the brace assembly on the leg. The securing strap is secured to both of the side brace elements at a securing point and can include a buckle 839 or other means to connect/couple the ends of the securing strap. It is understood that securing straps can be used on either the upper or lower portions or both portions. The securing strap may also be used around the front of the wearer's leg if necessary and can be positioned at various locations between the hinge and the distal end of the brace portions.

In one embodiment shown in FIG. 9, the brace assembly 900 with side brace elements can be integrated with embodiments similar to those shown in FIGS. 1A and 1B. As shown in FIG. 9, a shin shell 921 can be attached to portions of the elastic cross strap 960 so that the shin shell provides some protection to the shin of the wearer. As shown, the upper shaped edge 927 of the shin shell in embodiments can be shaped to align with the exterior shape of the tibial tubercle of the knee. As described above, the shin shell can also be made of a flexible material or when desired, it can be made of more rigid material to provide some tibial protection to the wearer.

One embodiment of the brace assembly further comprises configuring the tibial pad to function as an endo-skeleton such as with a wearer's shin guard, as may be required in a sport such as soccer, to support anterior tibia and anterior drawer control. FIG. 9 shows the shin shell attached to a shin guard 929.

Although not necessary, it is contemplated that some embodiments of the assembly can be capable of being integrated with a patellar control-open patellar donut as prescribed. In these embodiments, the assembly may include straps for patellar subluxation that stabilizes the elastic cross strap or hinges.

Although the above description and terminology of the components of the embodiments above utilize the terminology of a knee, it is understood and contemplated that the assembly can be applied to other joints. For example, and not for limitation, embodiments of the assembly can also be used with a person's elbow, back, shoulder or ankle. Such embodiments of the brace assembly are shown in FIGS. 12-16. For these other embodiments, the terms "upper" and "lower" such as in describing the mounting units, are still used to mean mounting units on sides of a joint whether they are on opposite sides or relatively higher or lower relative to the joint or not. For example, in braces used for a shoulder, the upper mounting unit can be mounted about the torso or shoulder of the wearer and the lower mounting unit can be mounted around the humerus. Similarly, in braces for an elbow, the upper mounting unit can be mounted about the humerus and the lower mounting unit can be mounted about the radius and ulna. In braces for an ankle, the upper and lower mounting facilities may both be above the ankle, but the brace may still function satisfactorily.

Additionally, for some of these alternative embodiments for joints other than knees, it is understood that the general description of the placement of the brace elements about the joint accommodates different joints and accommodates the extension/flexion resistance the brace is intended to provide. Posterior placement of the cross origin generally means on the opposite side of the extension or flexion that the brace is resisting and anterior placement of elements such as resistance points is on the same side of the body part going into extension or flexion. For example, the posterior placement of the cross origin is on the opposite (posterior) side of the extension of the elbow even though that side of an arm is generally anterior to the wearer's body when the arms are down. Similarly, the resistance points of the brace are on the same side as the extension even though that side of the arm is typically on the posterior side of the wearer's body.

Figure 12A:
FIGS. 12A-12F illustrate different views of embodiments of an ankle brace assembly.
Figure 12B:
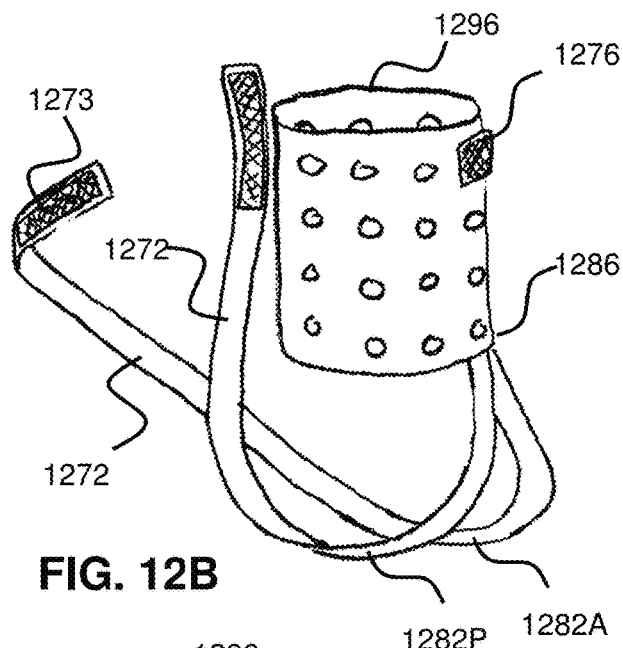
Figure 12C:
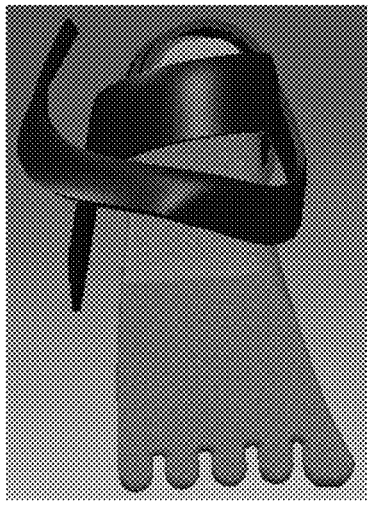
Figure 12D:
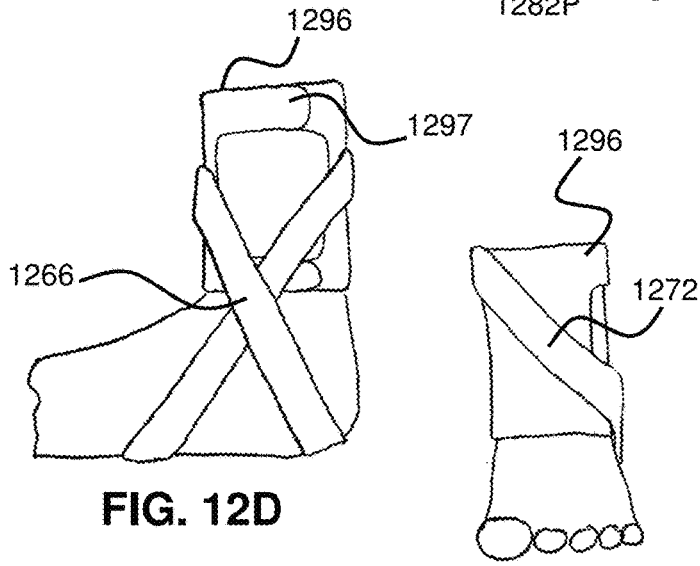
Figure 12E:
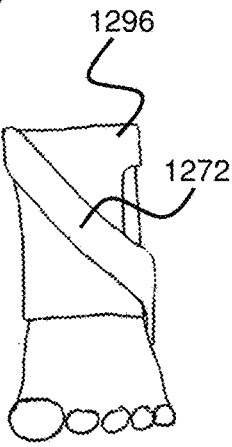
Figure 12F:
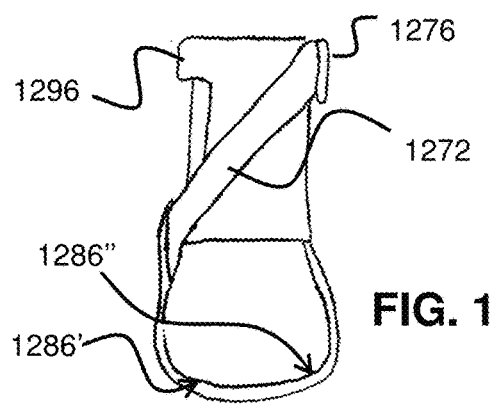

FIGS. 12A-12F illustrate one embodiment of a brace to be used on an ankle. In this embodiment, as shown in FIG. 12A, a single flexible sleeve is wrapped tightly around the lower portion of the leg above the ankle with two straps extending from the lower portion of the sleeve. The cross strap arms extend from the lower attachment point of the sleeve (lower mounting facility) through the cross origin and back to the upper attachment point of the sleeve (upper mounting facility). As illustrated in FIG. 12B, the lower portion of the cross strap arms 1282 extend from the lower attachment point 1286 and the upper portion of the cross strap arms 1272 are attached to the upper attachment point 1276 at the upper portion of the sleeve 1296 through an attachment means 1273 such as, but not limited to hook and loop fasteners, clips, buttons, snaps or any other method of attaching. FIG. 12C illustrates how the cross strap arms are positioned under the foot of the wearer. FIG. 12D shows how the cross straps form the cross origin 1266 on the lateral ankle. FIG. 12E shows a front view of an installed brace showing how one cross strap 1272 passes anterior to the leg to attach medially to the brace upper attachment point. FIG. 12F illustrates a rear view of an installed brace showing one cross strap 1272 passing posterior to the leg and attaching medially to the brace upper attachment point 1276. The positioning of the brace elements as shown, help rolling of the ankle from outside to inside. Although the eventual lower attachment point for the strap is above the ankle in some embodiments, the point of resistant force (as described above in FIG. 3A-3B) for the lower portions of the cross straps can be at a point proximal to the bottom of the wearer's foot. In this embodiment, because of the relative location of the upper and lower attachment points relative to the cross origin, the angles between the attachment points about the cross origin can be different than in other embodiments and still provide satisfactory results.

In some embodiments for the ankle, the lower mounting facility or the lower attachment point can located at or near the bottom of the wearer's foot. For these embodiments, the mounting facility may be a frictional engagement of the strap with the bottom of the foot or an additional element such as a sole pad that also attaches to the strap.

Another embodiment could include a non-elastic portion of the cross strap that extends from the bottom of the sleeve to a point proximal to the sole of the foot such that the attachment of the non-elastic portion of the strap to an elastic portion functions as the lower attachment point. An embodiment of this type may be configured so that the lower resistance point is about where the sole of the foot transitions to the medial inside of the foot.

In some embodiments of the ankle, the brace can be positioned such that the cross origin is on the medial ankle to prevent the rolling of the ankle from the inside to out. It is also contemplated that the brace can be configured so that cross strap create a cross origin on the lateral ankle as well as create a cross origin on the medial ankle to help resist rolling of the ankle in either direction.

Although the embodiment in FIGS. 12A-12D resist rolling of the ankle, it is understood that other embodiments can be used to resist other movement of the ankle. For example and not for limitation, the cross origin can also be placed above the area of the talus bone of the ankle with the upper attachment point being at a position posterior to the tibia and the lower attachment point being near the bottom of the foot to help resist dorsiflexion of the ankle.

Additional brace embodiments for the ankle are contemplated that include cuffs, frames, sleeves, hinges, struts and other elements as described herein.

Figure 13A:
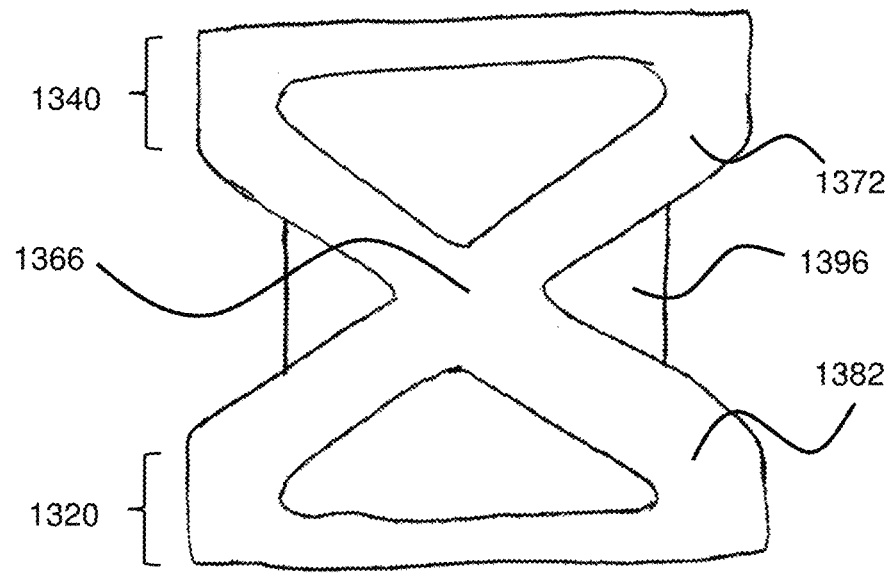
FIGS. 13A-13B illustrate one embodiment of a brace assembly for a wearer's back.
Figure 13B:
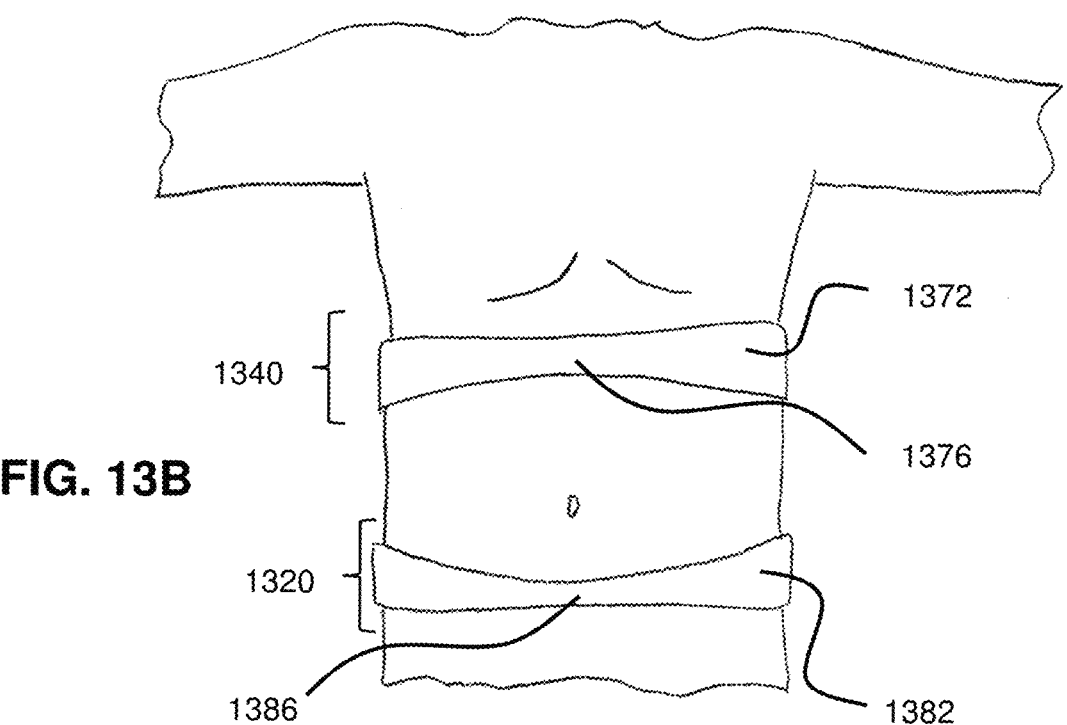

FIGS. 13A-13B illustrate an embodiment of the brace for a wearer's back where the back is viewed as a joint. FIG. 13A illustrates a rear view of a brace having a frame 1396 and a cross brace having a cross origin 1366, arms 1382 and 1372 and the arms creating the upper and lower mounting facilities 1340 and 1320. The frame helps guide the cross strap arms and provide some rigidity to help the mounting facilities and attachment points maintain their position on the back. The positioning of the cross origin in the small of the wearer's back helps resist bending forward of the wearer. As illustrated in FIG. 13A, it is understood that the cross straps can be integrated into portions of the frame (as shown) as well as be separate straps interoperating with the frame. FIG. 13B shows how the brace is mounted from the front of the wearer with the attachment points 1376 and 1386 being where the straps attach to themselves as the upper and lower mounting facilities. Additional embodiments for the back are contemplated that include cuffs, frames, sleeves, hinges, struts and other elements as described herein.

Figure 14A:
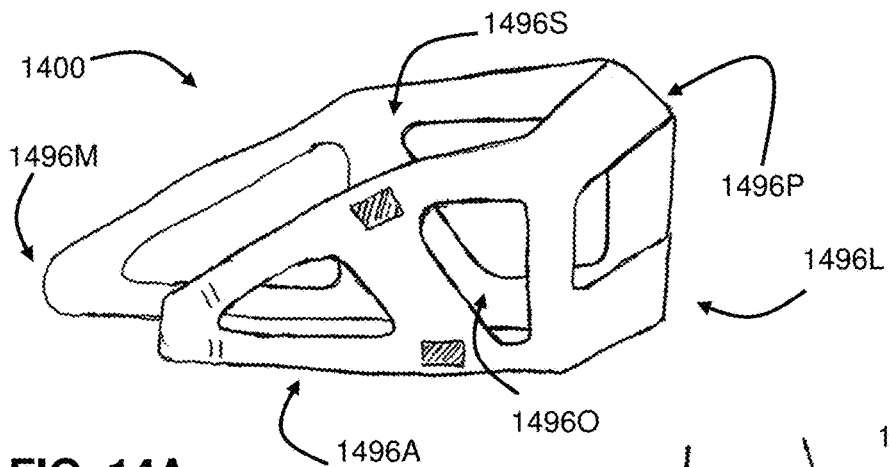
FIG. 14A-14C illustrate one embodiment of a brace assembly for a wearer's shoulder.
Figure 14B:
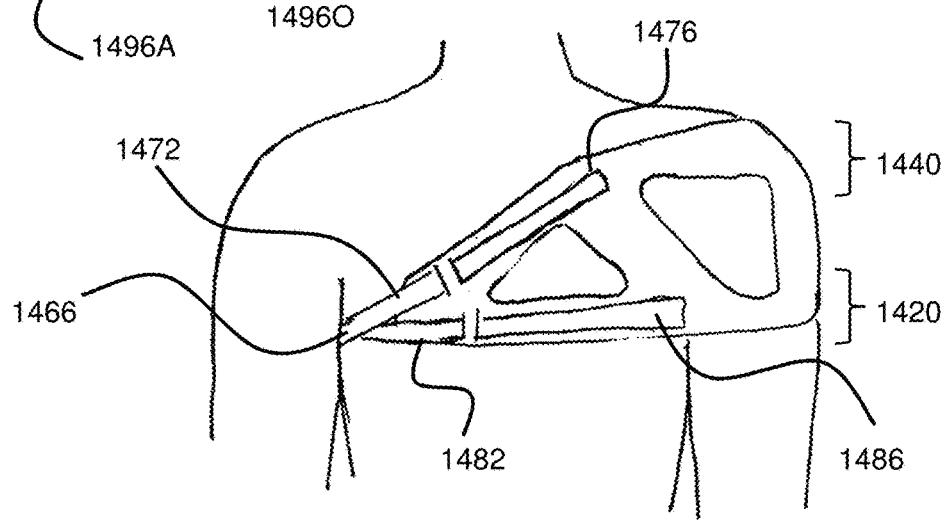
Figure 14C:
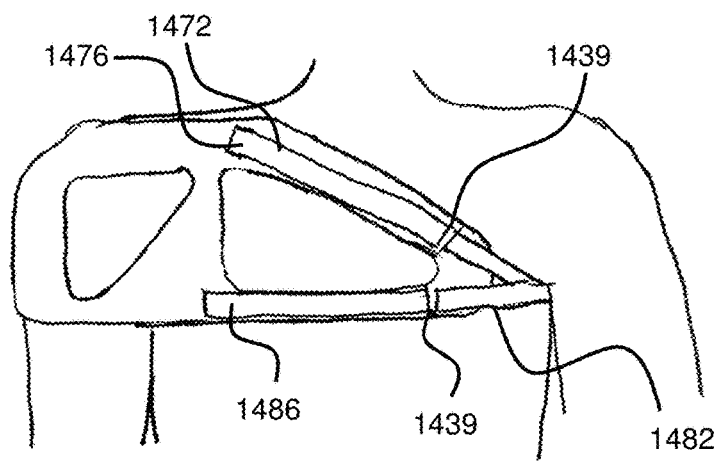

FIGS. 14A-14C illustrate one embodiment of the brace for a wearer's shoulder. As shown in FIG. 14A, the brace has a frame and attachment points for an elastic cross strap. The frame has a medial 1496M, lateral 1496L, anterior 1496A, superior 1496S and posterior 1496 (behind) portion. There are various openings 14960 designed into the brace for wearer comfort but still allow for the proper transfer of force within the brace. The positioning of this brace helps resist abduction and external rotation of the humerus. As shown in FIGS. 14B and 14C, the cross strap is configured such that a cross origin 1466 is positioned across the torso from the shoulder being braced. In this example embodiment, the cross origin is about in the axillary fossa of the user's opposite shoulder. As shown in the front view of FIG. 14B, from the cross origin 1466, cross strap arms 1472 and 1482 extend towards and attach to the attachment points 1476 and 1486 on the portion of the brace functioning as the upper mounting facility 1440 and the lower mounting facility 1420. As shown, the upper mounting facility is located above the shoulder joint and the lower mounting facility is located below the shoulder joint. As shown in the rear view of FIG. 14C, and consistent with the other descriptions herein, the cross strap arm 1472 that is attached to the lower attachment point in the front is the cross strap arm 1472 that is attached to the upper attachment point 1476 in the back and vice versa. Although not required, this embodiment contains guide rings 1439 through which the cross strap arms pass on the anterior and posterior portion of the brace to help guide the cross strap arms. Additional embodiments for the shoulder are contemplated that include cuffs, frames, sleeves, hinges, struts and other elements as described herein.

Figure 15A:
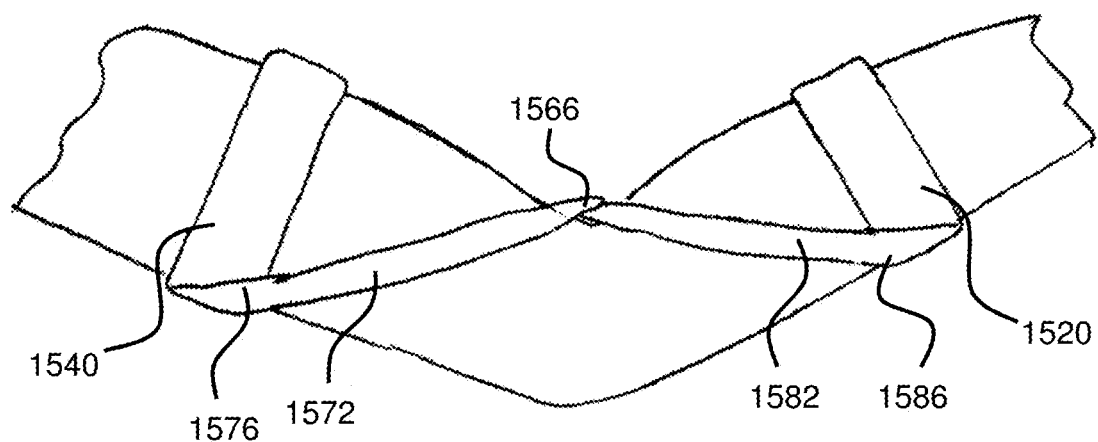
FIG. 15A-15B illustrate one embodiment of a brace assembly about a wearer's elbow.
Figure 15B:
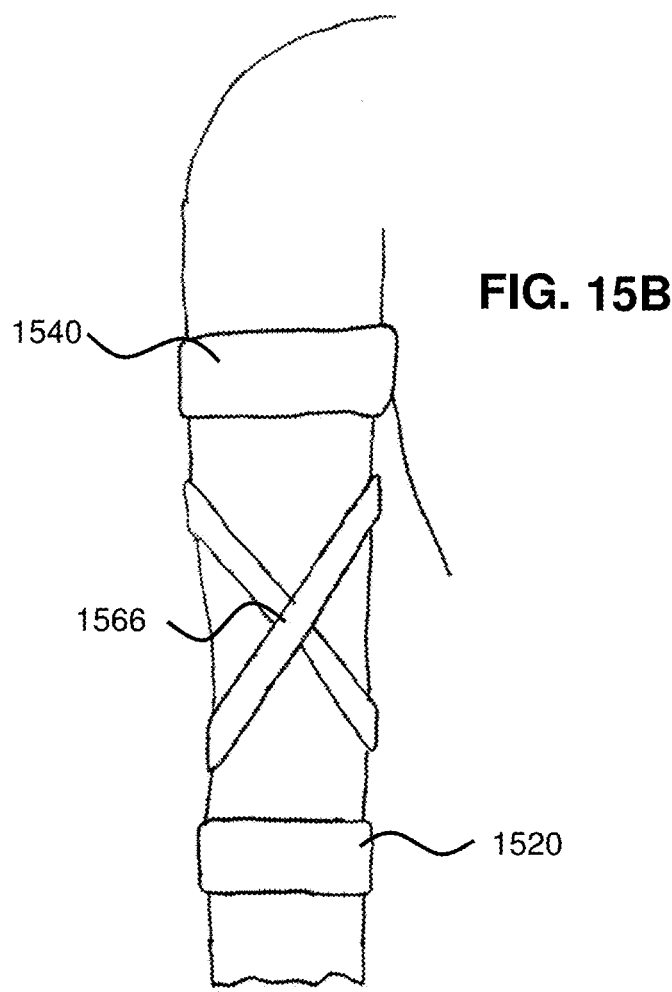

FIGS. 15A-15B illustrate one embodiment of the brace for a wearer's elbow. As shown in FIG. 15A, the brace has a cross brace having a cross origin 1566, cross strap arms and the arms create the upper and lower mounting facilities 1540 and 1520. The positioning of the cross origin in the antecubital fossa of the elbow and the strap attachment points on the other side of the arm helps resist hyperextension of the elbow. Additional embodiments for the elbow brace are contemplated that include cuffs, frames, sleeves, hinges, struts and other elements as described herein.

Figure 16A:
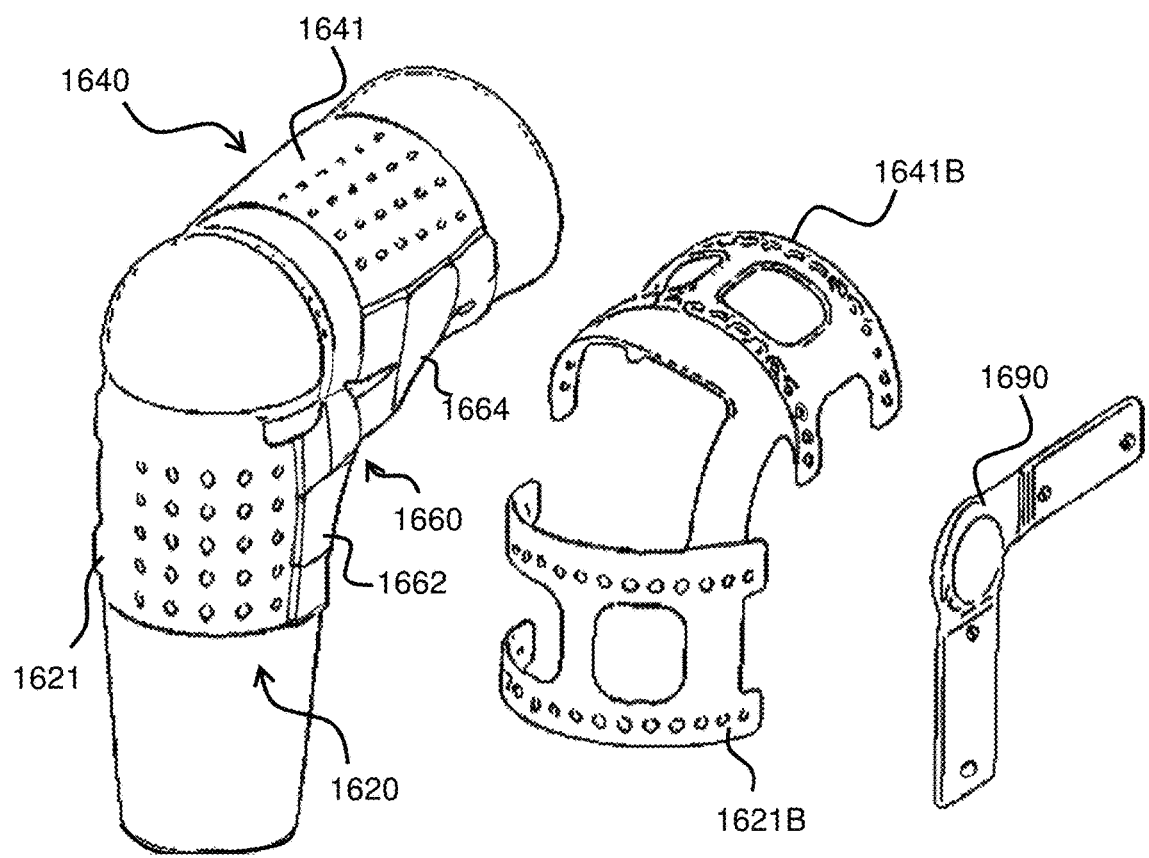
FIG. 16A illustrates an exploded view of another embodiment of a brace for a wearer's knee.
Figure 16B:
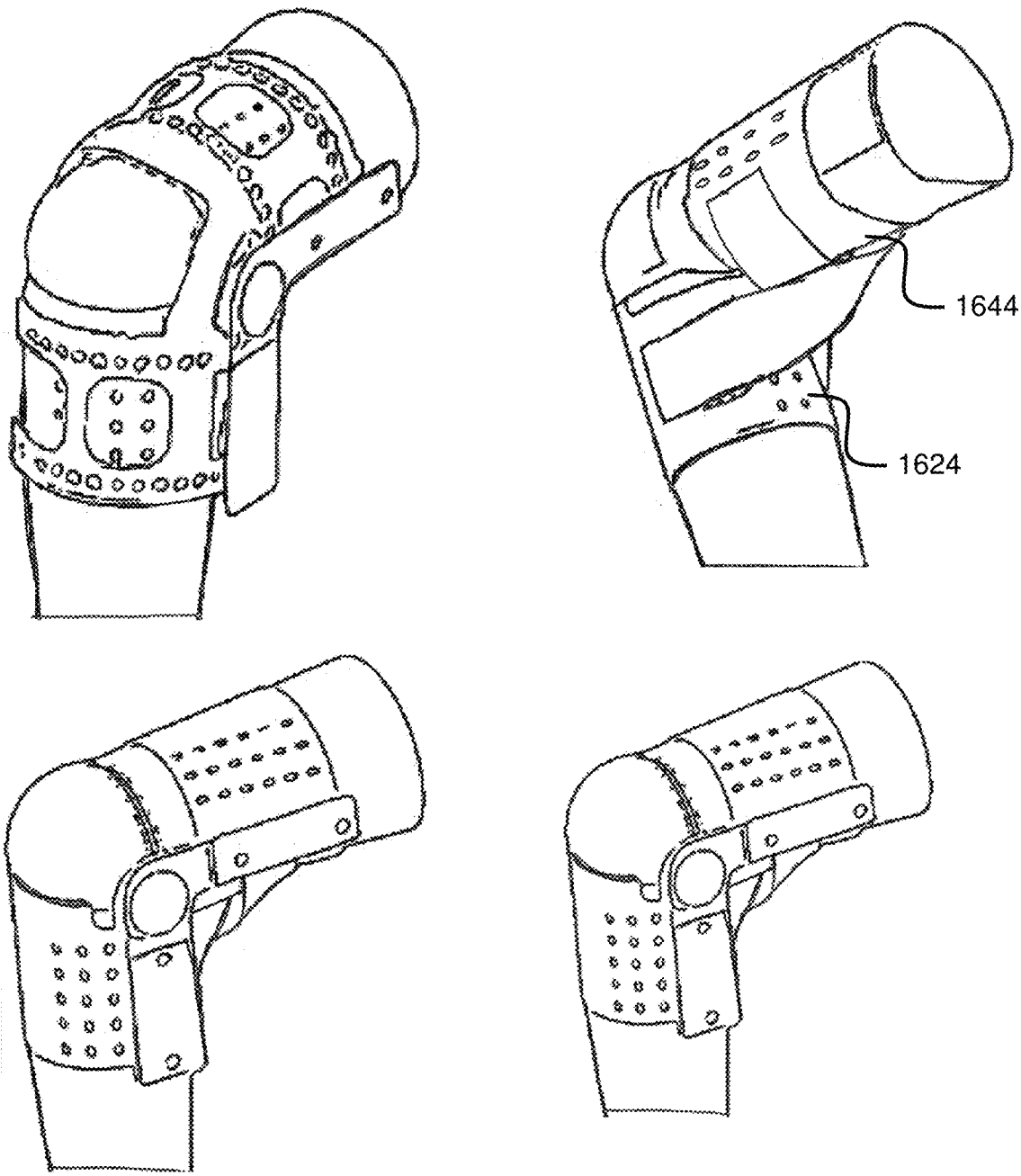
FIG. 16B illustrates different views of the embodiment of FIG. 15A for a wearer's knee.

FIGS. 16A-16B illustrate another embodiment of the brace for a wearer's knee. As shown in FIG. 16A, this embodiment has a cross strap brace with an upper mounting facility 1640, lower mounting facility 1620 and a cross strap 1660 configured to create a cross origin behind the wearer's knee to resist hyperextension. The cross strap 1660 may comprise multiple cross straps as shows 1664 and 1662. The upper mounting facility 1640 comprises an upper cuff 1641 with a portion of the cuff functioning as a strap (shown in FIG. 16B as 1644) to secure the upper cuff 1641 to the leg. The lower mounting facility 1620 comprises a lower cuff 1641 with a portion of the cuff functioning as a strap (shown in FIG. 16B as 1624) to secure the lower cuff 1641 to the leg. This embodiment may optionally also comprise an additional upper cuff brace 1641B, a lower cuff brace 1621B and a hinge 1690 capable of connecting the cuff braces. FIG. 16B illustrates how elements of this embodiment are positioned relative to each other and the wearer's knee.

Figure 17A:
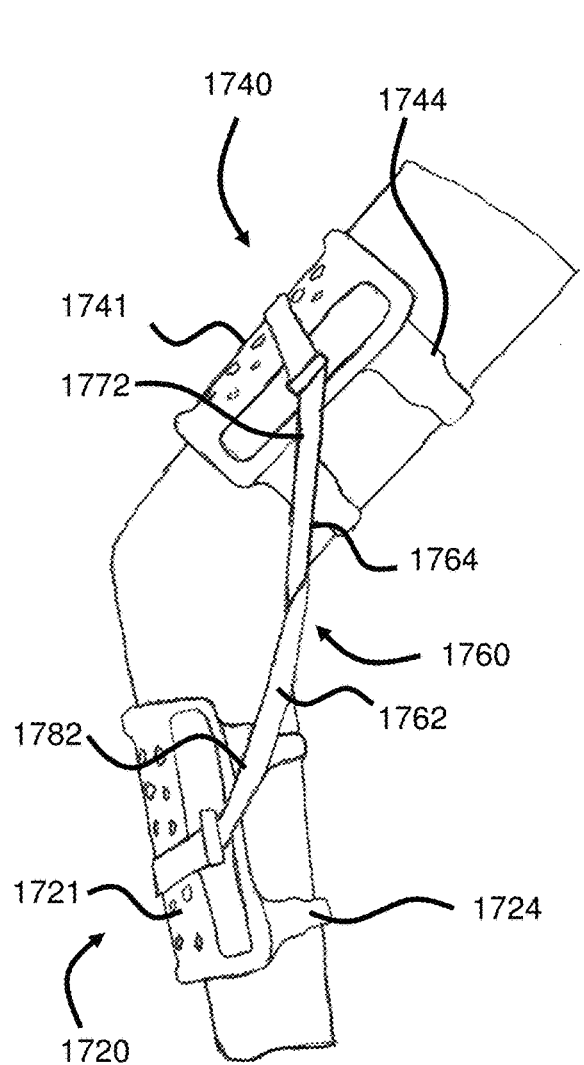
FIG. 17A illustrates a medial view of an example embodiment of a brace for a wearer's knee.
Figure 17B:
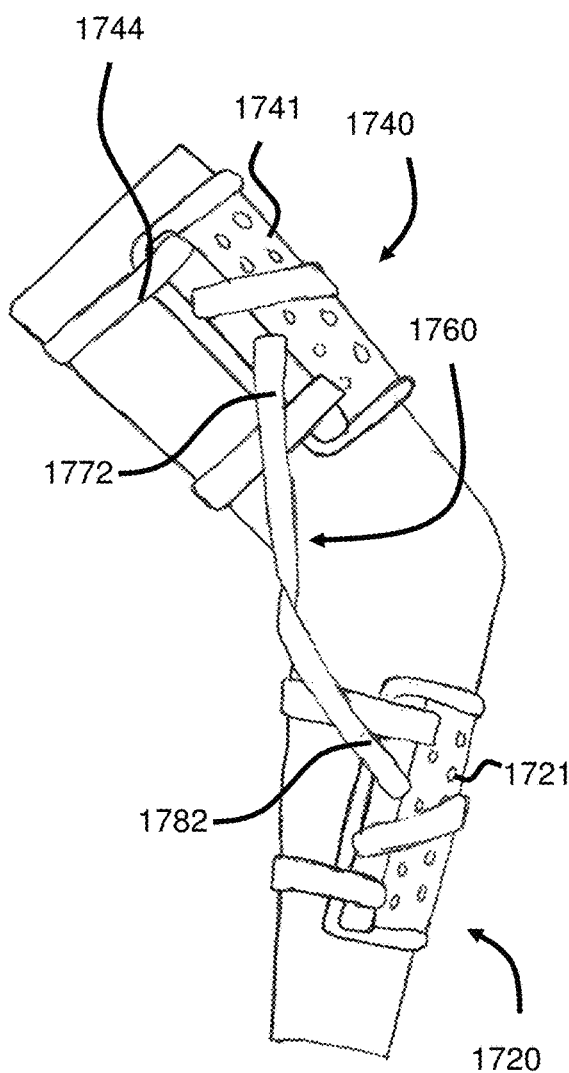
FIG. 17B illustrates a lateral view of an example embodiment of a brace for a wearer's knee.

Additional embodiments of the elastic brace assembly are shown in FIGS. 17A-17F and 18. Although these example embodiments are illustrated through the use of the elastic brace assembly on a knee joint, it is understood that some of these embodiments, as some of the above embodiments, may also be used on other joints such as but not limited to the back, ankle, shoulder and elbow. Referring to FIGS. 17A-17D, in these additional example embodiments, the elastic hyperextension cross strap 1760 comprises two elastic straps 1762 and 1764 each having an upper arm 1772 and a lower arm 1782. The upper mounting facility 1740 comprises an upper elastic pad/cuff 1741 and one or more elastic securing straps 1744 to secure the upper elastic pad to the leg. The lower mounting facility 1720 comprises a lower elastic pad/cuff 1721 and at least one elastic securing strap 1724 to secure the lower elastic pad/cuff 1721 to the lower leg. The elastic hyperextension cross straps 1762 and 1764 attach to the upper and lower mounting facilities whereby the elastic cross straps provide progressively increasing resistance to the extension of the user's knee when the elastic cross straps are properly positioned posterior to the user's knee. In some embodiments, as shown in FIG. 17B, the elastic cross strap is coupled to the mounting facilities as an attachment point lateral or medial to an anterior point of the mounting facility. As shown, lower arm 1782 is attached to a point of the lower mounting facility 1720 at a point lateral to the anterior point of lower mounting facility 1720. Although not required, in these embodiments, the upper and lower mounting facility are separate elements defined by portions of brace elements cooperating with the elastic cross strap.

FIGS. 17C and 17D further illustrate example embodiments as viewed from positions posterior and anterior to the brace worn on a knee. As shown in FIG. 17C, some embodiments also include an additional guide 1749 and 1729 through which the arms of the cross straps pass to help keep the cross straps positioned during use. The guides 1749 and 1729 may be part of the cuffs 1741 and 1721 or they may be part of reinforced guide pads 1749P and 1729P as shown. The guide pads may be made of the same material as the upper and lower cuffs and be removably or permanently coupled to the cuffs.

Figure 17E:
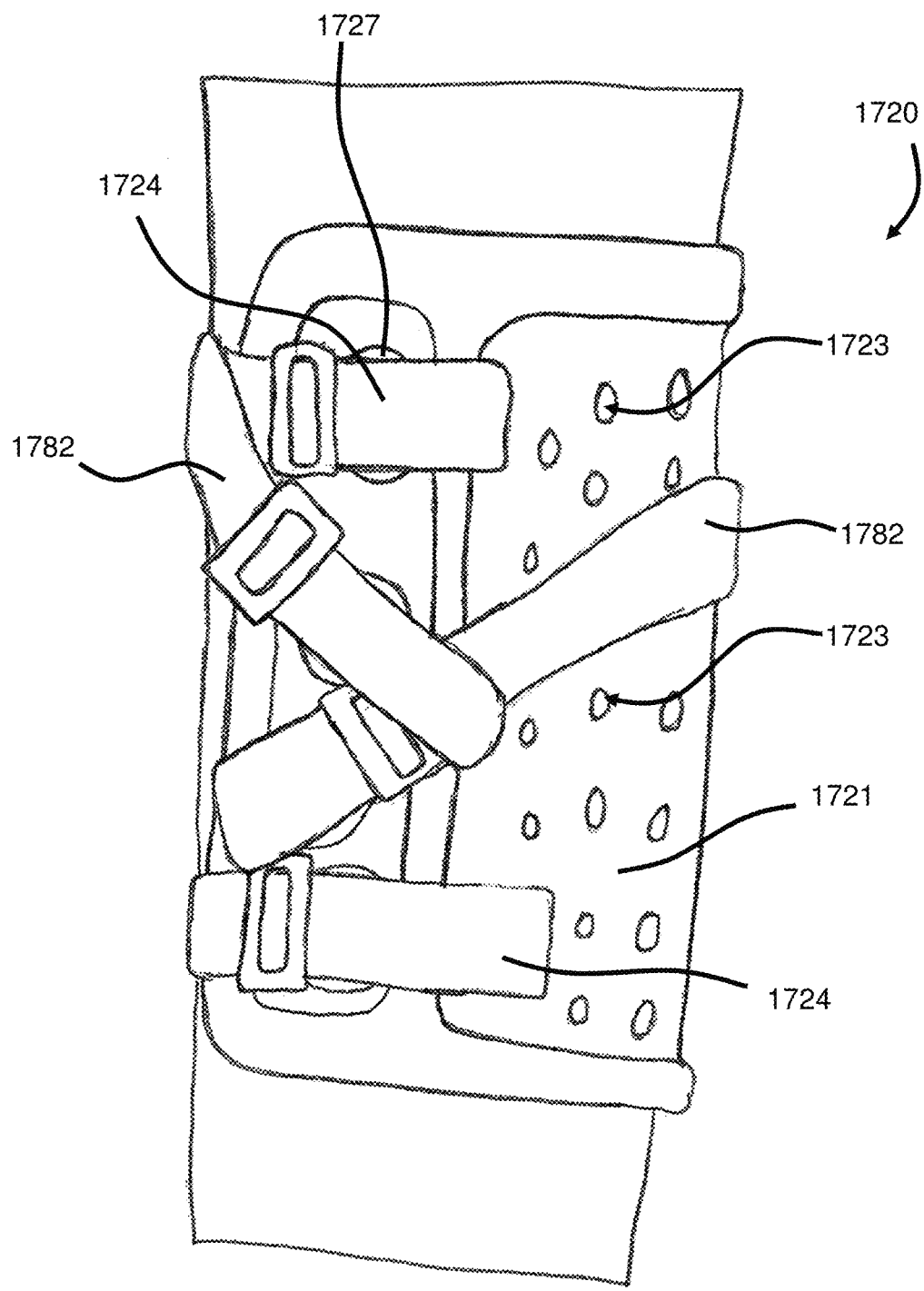
FIG. 17E illustrates a lateral view of an example embodiment of lower mounting facility for a brace for a wearer's knee.

Referring to FIG. 17E, the lower mounting facility 1720 comprises a lower pad/cuff 1721 which may have interspaced openings 1723 through the thickness of the cuff. As shown, one embodiment of the openings 1723 are through holes extending through the thickness of the mounting facility to increase friction and to allow perspiration to escape from under the mounting facility. Also shown in this embodiment are strap buckles 1727 to secure the straps 1724 to the mounting facility. Suitable buckles 1727 for embodiments include, but are not limited to, those disclosed in pending U.S. patent application Ser. No. 13/654,476 filed on Oct. 18, 2012 and US Pub. No. 20130097826 published Apr. 25, 2013, which is herein incorporated by reference in its entirety.

Figure 17F:
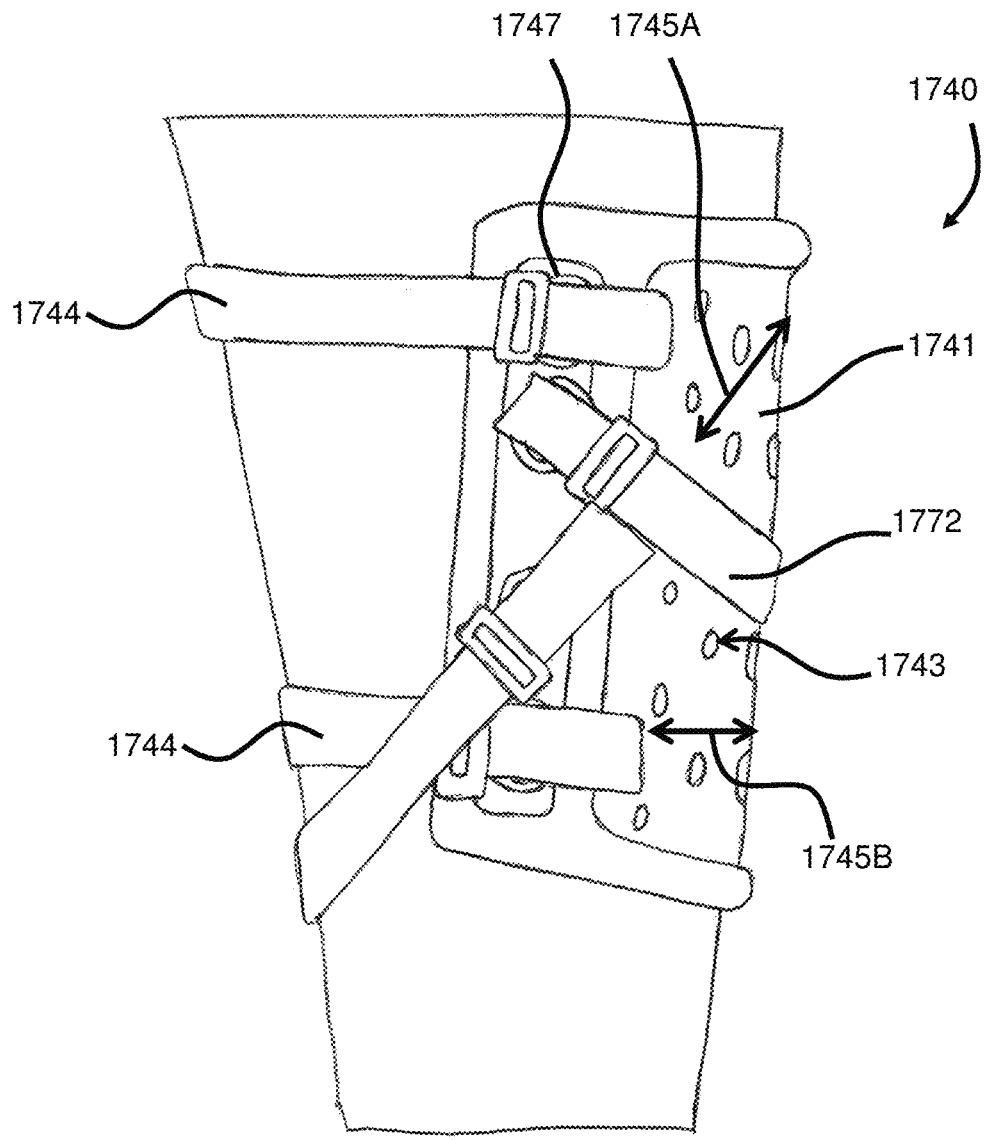
FIG. 17F illustrates a lateral view of an example embodiment of an upper mounting facility for a brace for a wearer's knee.

Referring to FIG. 17F, the upper mounting facility 1740 comprises an upper pad/cuff 1741 with interspaced openings 1743 through its thickness. The openings 1743, buckles 1747, upper arms 1772, securing straps 1744 and other similar elements may be configured to function similar to those described for the lower mounting facility.

As shown in FIGS. 17A-17F, the mounting facilities may have openings that provide comfort and friction features such as an ability for the skin under the mounting facility to have some exposure to the outside environment and to provide some irregular surfaces on the inside of the mounting facility to increase friction with the skin and/or underclothing. As detailed in FIG. 17E, the openings 1743 may also be aligned in a manner such that the mounting facility still has non-intermittent and continuous "strips" of mounting facility material (between and uninterrupted by openings) extending along and in alignment with the direction of the resistance force that is put onto the cuff by the elastic hyperextension cross strap and/or the elastic securing straps. Arrows 1745A and 1745B show examples of these strips of continuous material.

In some embodiments, when the elastic cross strap is attached to the mounting facility at an attachment point that is a distance from the resistance point, the strips of mounting facility material are able to function as extensions of the elastic cross strap and extend the material providing the resistance force to a more ideal resistance point. For example, if the elastic cross strap was to attach to the mounting facility on a generally medial or lateral position around the knee of a leg, the continuous strips of mounting facility material may extend upward or downward from the attachment point to an anterior point on the leg and allow the resistant point of the brace to be higher and lower on the joint and in a more anterior position. The pads/cuffs may also be made from a non-elastic materials or an elastic material, similar to the elastic cross strap that allows the continuous strips to extend the elastic properties of the elastic cross strap. This can be done consistent with and with similar "strips" of mounting facility material allowing the mounting facility to provide resistance to the elastic securing straps.

The elastic cross straps may also be configured with openings. The openings in the cross straps may provide similar comfort and friction benefits as do the openings in the mounting facilities. In addition, the openings in the cross strap may allow for one design of a strap to have different resistance properties based on the size and/or the shape of the openings. For example, a similar elastic cross strap design can be made to have two resistance properties by having one size openings for one configuration and have less resistance by having larger sized openings (across the width of a strap designed to provide resistance along its length) for another configuration.

FIGS. 17A-17F also show example embodiments of buckles that may be used to attach or couple the elastic cross straps and securing straps to the pad/cuffs. The example buckles have mating elements with one secured to the strap and another element secured to the pad/cuffs. The elements on the straps allow the element to be adjusted along the length of the strap to adjust the effective length of the strap and therefore alter the resistance properties of the strap when both ends of the strap are attached to the brace assembly. As shown, the buckles may be arranged at predetermined angles that correspond to the angles of the strap attachments.

Figure 18A:
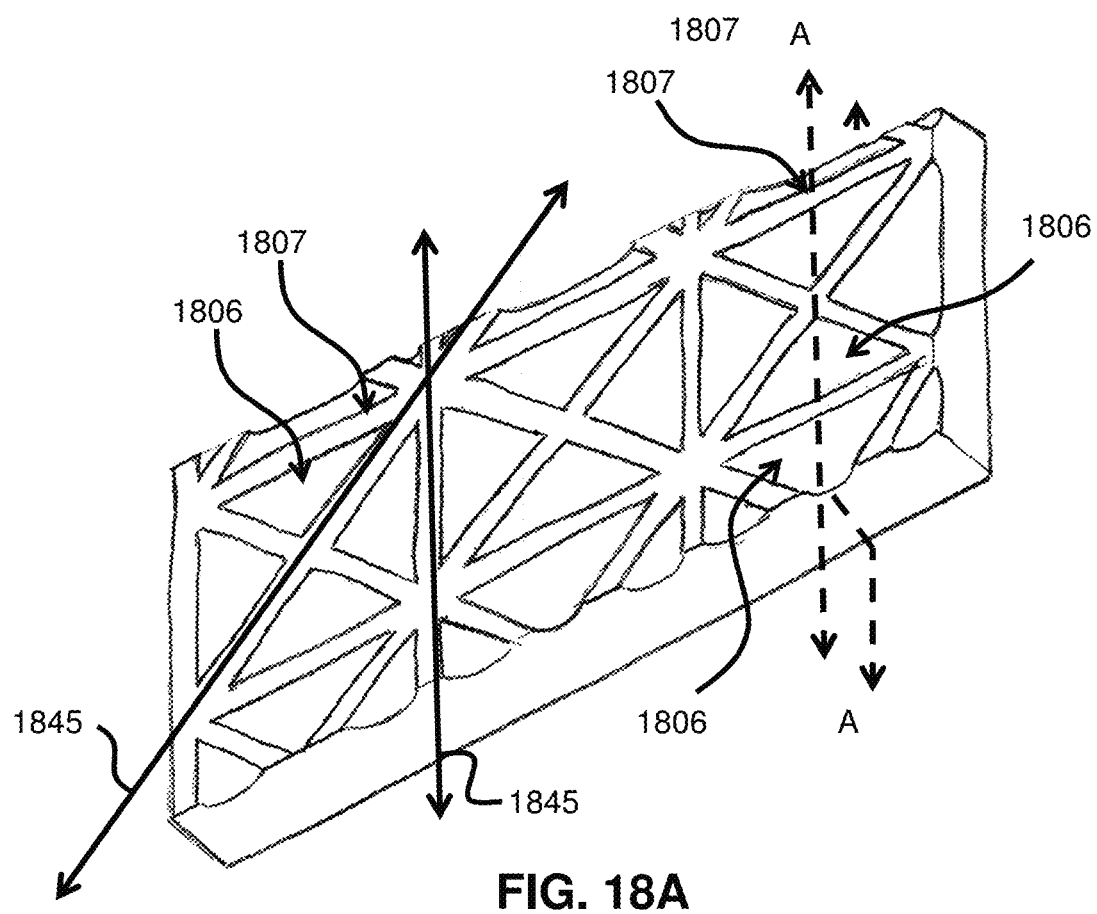
FIG. 18A illustrates one example embodiment of the under surface of a mounting facility material showing diamond shaped indentations between a flat surface, here an interlaced flat surface, that increases the friction of the brace element with the user's skin or underclothes.
Figure 18B:
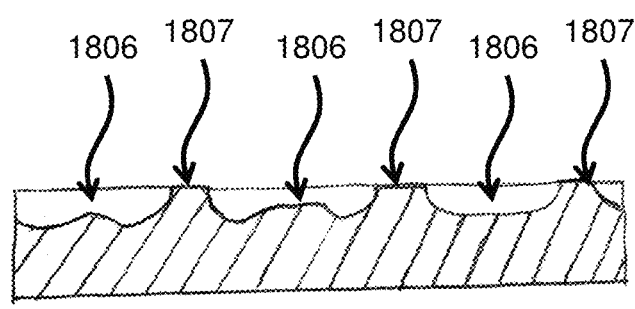
FIG. 18B illustrates a cross-sectional profile of the mounting facility material of FIG. 18A.

Referring to FIGS. 18A and 18B, one embodiment of an inner surface of brace elements is shown where the inner surface is designed to enhance the frictional engagement of the brace with the skin or underclothing of the user. As shown, the elastic material has a multiple of faced diamond shaped indentations 1806 between a generally planar surface, here an interlaced flat surface 1807, that increases the friction of the brace element with the user's skin. The diamond shaped indentations 1806 create an irregular surface and an increased surface area of the inner surface against the skin or underclothing. Additionally, the indentations 1806 allow a portion of the skin to occupy some of the space of the indentation and this irregular surface of the skin also increases the friction of the skin against the brace inner surface. As shown, the alignment of the flat surfaces 1807 may provide the non-intermittent and continuous strips of material (along arrows 1845) extending along and in alignment with the direction of the resistance force that is put onto the material to extend and/or enhance the resistance properties of the brace assembly elements. FIG. 18B shows a cross-sectional view of the material of FIG. 18A at section A-A. FIG. 18B illustrates the indentations 1806 and the raised surface 1807. In some embodiments, the indentations may be substituted or combined with through hole openings to enhance the frictional engagement of the material and to enhance breathability of the cuff and assembly.

These embodiments are capable of providing a dynamic elastic brace assembly that protects the knee by keeping it in an 'athletic position' protecting the ligaments and allowing the muscles around the knee to stabilize while protecting against muscle atrophy. These embodiments may be an alternative to taping the joint whereby there is no need to re-apply loose tape between events and no more costly continuous tape purchases. These embodiments provide an alternative to functional braces providing less slippage due to heavy, rigid structures and reduced skill limitations. Embodiments may provide extension prevention like a rigid brace but with the comfort and normal control of a taping procedure. Embodiments may be capable of being designed without metal and therefore may be used in sports that do not allow metal braces.

Embodiments may be less costly, lighter weight, can be loosened between break times, intermissions and time-outs. Embodiments may control against knee hyperextension; a major cause of ACL tears and failure of ACL surgical repairs. Embodiments may control hyperextension by gradually increasing resistance such that the athlete experiences a "soft stop" which is more comfortable and doesn't shift the brace down the leg like a normal metal brace with hinges that creates a "hard stop". Embodiments may mimic taping procedures that have been proven to outperform expensive functional braces. Embodiments may be less expensive and less irritating than repeatedly taping the knee or purchasing a custom fit or off-the shelf functional brace for sports, thereby increasing the number of athletes of all ages that can protect their knee during sports. Embodiments may be used as a training brace by adding a hip rotation strap that will teach athletes how to properly jump and land without tearing their ACL. Embodiments may be easily removed or partially released during short and long rest periods during athletic events, unlike functional braces that have to remain applied and often taped in place to prevent slippage. Embodiments may be applied to all leg shapes and sizes without losing its effectiveness. Many body types and heavy people cannot wear a functional knee brace. Embodiments may be used on both knees at the same time for training and preventative use.

Embodiments may also increase quadriceps muscle strength because they provide resistance to extension. Embodiments may be light weight and easy to apply. Embodiments may allow the elastic/dynamic cross straps to be inexpensively replaced after multiple uses or breakage thus maintaining the active control of knee motions. Embodiments can act as the foundation to add accessory pieces that will protect against side blows (hinged lateral paddle), unstable knee caps (lateral buttress), or shin guards for soccer and motocross. Embodiments may be comfortably worn under pants or athletic gear. Embodiments may be worn during skiing without requiring shorter ski boots or shorter less effective braces.

In addition, embodiments may further include additional features such as, but not limited to: side paddle with a hinge that can be added for lateral support, breathable over-sleeve, hip rotation training strap and different colors.

Embodiments of the elastic brace assembly may be utilized as a hyperextension prevention brace where it may prevent hyperextension of the knee during activity, they may be used as a training brace for practice or game keeping the knee in a "athletic" position, and they may be used in sports in which braces with any metal can't be used (e.g., soccer, etc.).

Embodiments of the elastic brace assembly may be utilized as a hyperextension prevention brace with hinges. Embodiments may be unilateral or bilateral. Embodiments may maintain position of brace on the knee sliding due to the elastic cross straps. Embodiments may be used as postoperative hyperextension prevention for ACL surgery.

Embodiments of the elastic brace assembly may be utilized as a hyperextension patellar-femoral brace. Embodiments may apply a hinge unilaterally or bilaterally with extension stops and the elastic cross strap design to help position the knee for patellar tracking in the grove. Embodiments may apply lateral buttress and straps to apply medial force to the patella.

In other embodiments, the proximal and distal straps may be wider than shown, about three inches (3") that wrap around the front and then attach to help hold the mounting facilities down. In some embodiments, the stabilizing straps also may be longer and wrap around the anterior of the limb and then attach to help hold the mounting facilities on the limb. In some embodiments, the elastic cross straps may be moved to the most distal position with the angle of the buckle changed to align with the direction of the strap. In some embodiments, conform tape may be used on the skin to enhance the interface with the brace.

Although not necessary, in some embodiments of the assembly, the assembly further includes a covering that can be decorative and/or can provide a sleek/smooth surface for the wearer.

One Embodiment of the Brace Assembly in Operation:

One embodiment of the disclosed inventions will be used to further illustrate the operational aspects of the invention. Although the embodiment discussed utilizes an assembly embodiment with a shin shell as the lower mounting facility, it is understood that embodiments of the invention may be applied to an assembly without a shin shell. For those other embodiments, such as shown in FIG. 5, the attachment of the straps on or around the wearer's thigh in a sleeve provides many of the same functions as the upper mounting facility described below.

One embodiment of the invention, as shown in FIGS. 1A and 1B, is used about a wearer's knee 105. The brace assembly 100 is initially secured on the wearer's shin 102. This is done by securing the shin shell 121 on the shin 102 and wrapping the securing straps 124 around the calf. This securing is done at a point of that calf such that the movement of the shell towards the knee is minimized. Once secured on the shin, the elastic cross strap arms 162 and 164 are wrapped behind or posterior to the knee creating an x-pattern as the cross origin 166 in the popliteal fossa of the knee and then wrapped anterior and around the thigh. The cross strap arms are wrapped so that one arm wraps from the lower attachment point 122 laterally, then behind the knee and then medial and upwards to the upper attachment point 142. The other arm wraps from the lower attachment point 122 medial, then behind the knee and them lateral and upward to the upper attachment point 142. Connectors 146A and 146B, such as Velcro, of the cross strap arms 162 and 164 are secured to each other forming the upper mounting facility 140. The upper arms of the cross strap are attached to matching Velcro fasteners on the cross strap such that they create facility attachment point 142 anterior on the thigh. As with the shin shell 121, the placement of the upper mounting facility 140 is done to minimize the movement of the facility towards the knee 105.

Once secured on the thigh 104 and the tibia, the presence of the elastic straps in the X configuration provides resistance to knee extension and helps prevent the knee from hyperextension. Hyperextension is prevented by the cooperation of the secured ends of the straps with the positioning of the straps behind the knee. The elastic properties of the cross strap can provide resistive properties early in the motion arch of the joint thereby help control extension early in the motion arch. As the joint extends, the elastic straps stretch and provide progressively more resistance. When the knee reaches a desired limit, the elastic straps reach a significant resistance level that prevents further extension. This resistance does not provide a hard stop of the extension. By not having a hard stop, brace migration is minimized as well as the discomfort caused by sudden jerking of the brace when the hard stop if reached. Additionally, this resistance approach uniquely provides therapeutic benefits such as increasing neuromuscular control and causing the extensor muscles to gradually strengthen which is beneficial for joint stability.

The point of attachment, facility attachment points 142 and 122, of the elastic straps and the thigh and tibial pad respectively are such that the desired resistance provided by the anterior resistance points allow proper knee movement but prevents hyperextension. Additionally, if the brace assembly 100 has good frictional contact with the skin, rotational support of the knee joint is also provided. As the wearer uses the brace assembly, and as their need for support and/or comfort changes, the elastic straps can be tightened or loosened to change the elastic tension on the system by simply removing and reattaching the straps with the Velcro attaching means.

The embodiment of FIG. 4 operates similar to FIG. 1. In this embodiment, the elastic cross strap 460 is used to function as both the lower mounting facility 420 and the upper mounting facility 440. This can start with the elastic cross strap being initially wrapped around the shin 402 of the wearer and crossing the arms around each other anterior to the shin. Once secured on the shin 402, the same methods described for FIG. 1 can be followed to mount the brace assembly on the knee. In this embodiment, the anterior resistance points are at points of the elastic cross strap at the front of the wearer's thigh and shin such as at strap attachment points 476 and 486.

The embodiment of FIG. 10 operates similar to the embodiments described for FIGS. 1 and 4.

Other Embodiments of the Brace Assembly in Operation:

The embodiments of FIGS. 2, 5 and 6 operate in a similar manner to those shown in FIGS. 1 and 4. With the embodiments of FIGS. 2, 5 and 6, the upper and lower cuff or the sleeve is mounted around the knee and the cross strap is attached to the attachment points and adjusted. The elastic cross straps can be adjusted so that the length of the upper and lower arms between the attachment points is made longer or shorter depending on the person wearing the brace assembly and the desired tension. In embodiments, the uprights can be contained within the under sleeve or other covering that connects the hinges to the upper and lower pad. The placement of the uprights maintain the relative distance between the upper and lower pad and therefore help maintain the resistance and support provided by the elastic straps.

The embodiments of FIGS. 7-9 operate similar to those in FIGS. 1 and 4. With the embodiments of FIGS. 7-9, the elastic cross strap can already be attached through the slots in the brace elements or it can be attached as part of putting the brace on by the wearer. The wearer puts their leg between the cross origin of the elastic cross strap and the portions of the elastic cross strap that become positioned on the front of the wearer's leg. The brace assembly is positioned so that the upper mounting facility is positioned above the joint and the lower mounting facility is positioned below the joint. The elastic cross strap is then adjusted with respect to the side attachment points by sliding the strap in and out of the slots. If necessary, the connectors on the end of the strap are unconnected to allow more adjustment of the strap. Once adjusted, the connectors are secured to each other so that the brace assembly is secured around the wearer's leg about the joint and provides the adequate amount of tension. If provided, the securing strap can be adjustably connected/coupled by a buckle to help further secure the brace on the wearer's leg. Once secured, the upper mounting facility is able to pivot about the hinge while the cooperation of the cross-origin with other portions of the elastic cross strap help prevent the wearer's knee from hyperextension.

The example embodiments illustrated in FIGS. 12A-12F operate in similar fashion to the embodiments already described. In this embodiment, the wearer positions a sleeve 1296 on the lower leg above the wearer's ankle joint. This may be positioned by sliding a closed sleeve (FIG. 12B) over the foot and the ankle or it may be positioned by wrapping an open sleeve (FIGS. 12A, 12D-12F) around the ankle joint and closing with closing means 1297 such as hook and loop type fasteners. The sleeve includes lower attachment points 1286 that attach two cross straps 1282A and 1282P with the sleeve medially at the lower attachment points 1286. The unattached ends of the two cross straps are then positioned about the wearer's foot and ankle. One cross strap, the anterior strap 1282A, is brought under the middle of the foot and back over the lateral ankle bone and brought behind the leg up to an upper attachment point 1276 on the sleeve on the lower leg. The upper attachment point 1276 is on a posterior or medial side of the lower leg. The other cross strap, the posterior strap 1282P, is brought under the heel of the foot, over the lateral ankle bone and brought in front of the leg up to an upper attachment point 1276 on the sleeve on the lower leg. The upper attachment point 1276 is on an anterior or medial side of the lower leg. This configuration positions the cross origin 1266 at a location on the lateral ankle bone and creates resistance points for the strap at both attachment points. To analyze the forces consistent with FIGS. 3A and 3B in this ankle joint embodiment, the upper attachment point 1276 represents the upper point of resistance, however the lower attachment point 1286 may not always define the lower point of resistance. The lower point of resistance, when the straps are frictionally engaged with the bottom of the foot, is the point where this frictional engagements starts along the strap from the cross origin such as 1286' and 1286". For embodiments with a mounting means under the foot as described earlier, the point at where this mounting means is attached to the strap may function as the point of resistance.

The embodiments of FIGS. 13A-13B start operation by positioning the frame portion 1396 on the back around the waist joint. Typically, this is positioned proximal to the lumbar area of the spine. Whether positioned already on the frame or separately, the cross strap arms 1382 and 1372 are configured on the frame such that the cross origin 1366 is positioned generally in alignment with, and in the middle of the lumbar area of the spine. In this embodiment, two cross straps extend from this cross origin, each having an upper arm 1372 and a lower arm 1382. The upper arm 1372 of a first strap extends up the torso to the right lateral side and wraps around the front of the wearer. The lower arm 1382 of the first strap extends down the torso to the left lateral side and wraps around the front of the wearer about at a waist position. The second strap has an upper arm extending up the torso to the left lateral side and wraps around the front of the wearer and the lower arm extends down the torso to the right lateral side and also wraps around the front of the wearer about at a waist position. The upper arms can be secured to each other creating the upper mounting facility 1340. The lower arms are also secured to each other creating the lower mounting facility 1320.

The embodiments of FIGS. 14A-14D utilize the cross strap to restrict the abduction and external rotation of the shoulder. This is typically configured by locating the point for the cross origin 1466 in the axillary fossa of the opposite shoulder. From this point, arms 1482 and 1472 extend across the torso and attach at attachment points 1476 and 1486 on the upper and lower mounting facilities respectively. These facilities are shown as being positioned on the upper shoulder above the joint and on the humerus below the shoulder joint. The arms of the straps are such that a continual strap extends from the upper mounting facility around the back, through the cross origin and around the front of the wearer to attach on the lower mounting facility. Another set of arms extend from the lower mounting facility around the back, through the cross origin and around the front of the wearer to attach on the upper mounting facility.

The example embodiments of FIGS. 15A-15B function similar to the knee embodiments except they are applied to the elbow joint. In these embodiments, the cross strap is configured such that the cross origin is positioned to resist extension of the radius and ulna relative to the humerus. This is typically configured by locating the point for the cross origin in the antecubital fossa of a wearer's elbow and having the cross strap arms extend up and down the arm of the wearer. As shown in the side view of FIG. 15A, the cross strap arms wrap around the upper part and the lower part of the arm such that the attachment points are on the opposite side of the arm from the antecubital fossa. In the embodiment shown, the cross strap is also wrapped around the arm to have that portion of the strap function as both the upper and the lower mounting facilities. FIG. 15B shows a front view of the elbow brace.

The embodiment shown in FIGS. 16A-16B operates similar to the other knee brace embodiments described above such as described for FIG. 2. Operationally, the cuff brace elements 1621B and 1641B as well as the hinge 1690 may be optionally provided and used to provide additional support for the brace.

The embodiments shown in FIGS. 17A-17F and FIG. 18 operate similar to the other brace embodiments described above such as described for FIG. 2.

For some embodiments, the length of the strap, and the tension put on the strap when attaching to the attachment points, can be varied to vary the resisting force on the joint utilizing attachment means described earlier.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

We claim:

1. A knee brace assembly comprising:
   an upper mounting facility for positioning the knee brace assembly about a thigh area of a user's leg;
   a lower mounting facility for positioning the knee brace assembly about a shin area of the user's leg;
   a cross strap having a cross origin;
   the cross strap being attachable to the upper mounting facility and the lower mounting facility whereby the cross strap limits an extension of the upper mounting facility and the lower mounting facility about the cross origin when the cross origin is positioned posterior to a user's knee in a popliteal fossa of the knee;
   the upper mounting facility having an upper mount front portion;
   the lower mounting facility having a lower mount front portion;
   the cross strap further comprising at least two upper arms to connect to the upper mounting facility at an upper attachment point on the upper mount front portion and at least two lower arms to connect to the lower mounting facility at a lower attachment point on the lower mount front portion;
   the cross strap having at least two lengths extending along each upper arm and each lower arm and between the upper attachment point and the lower attachment point;
   the cross strap comprising an elastic cross strap; and
   the knee brace assembly providing a resistance force to the extension without the use of a hinge.

2. The knee brace assembly of claim 1 wherein:
   the elastic cross strap comprises elastic material;
   the cross origin is configured to be positioned in the popliteal fossa of the wearer's knee; and
   the elastic cross strap is configured to provide a dynamic resistance force as the resistance force.

3. The knee brace assembly of claim 2 wherein the upper mounting facility and the lower mounting facility comprise an upper poriton and a lower portion of a sleeve having a flexible upright.

4. The knee brace assembly of claim 1 wherein the upper mounting facility and the lower mounting facility are operably connected by a flexible upright.

5. The knee brace assembly of claim 1 wherein:
   the cross-strap comprises at least two straps each strap having an upper end and a lower end;
   the two strap upper ends comprise the at least two upper arms and the two strap lower ends comprise the at least two lower arms; and
   the two straps are capable of being woven about the user's leg to create an x-pattern as the cross origin.

6. The knee brace assembly of claim 1 wherein:
   the cross strap comprises an x-shaped strap having the cross origin, the at least two upper arms and the at least two lower arms.

7. An elastic brace assembly for use by a wearer, the elastic brace assembly comprising:

an upper mounting facility and a lower mounting facility;
at least one elastic cross strap coupled to the upper mounting facility and the lower mounting facility;
the at least one elastic cross strap further forming a cross origin between the upper mounting facility and the lower mounting facility;
the elastic cross strap configured to form the cross origin in a fossa of the wearer's joint whereby the elastic cross strap provides a resistance force to an extension of the upper mounting facility and the lower mounting facility from the cross origin when the cross origin is positioned in a fossa of a wearer's joint;
the elastic brace assembly providing the resistance force to the extension without the use of a hinge;
the elastic cross strap is coupled to the upper mounting facility at an attachment point lateral or medial to an anterior point of the upper mounting facility; and
the elastic cross strap coupled to the lower mounting facility at an attachment point lateral or medial to an anterior point of the lower mounting facility.

8. The elastic brace assembly of claim 7 wherein:
the elastic cross strap comprises a elastic material;
the cross origin is configured to be positioned in the fossa of the wearer's joint; and
the elastic cross strap is configured to provide a dynamic resistance force as the resistance force.

9. The elastic brace assembly of claim 7 wherein:
the upper mounting facility comprises an upper portion of a sleeve;
the lower mounting facility comprises a lower portion of the sleeve; and
the upper mounting facility and the lower mounting facility are operably connected by a flexible upright.

10. The elastic brace assembly of claim 7 wherein:
the elastic cross strap is coupled to the upper mounting facility at an attachment point at an anterior point of the upper mounting facility; and
the elastic cross strap is coupled to the lower mounting facility at an attachment point at an anterior point of the lower mounting facility.

11. The elastic brace assembly of claim 7 wherein the elastic brace assembly is configured to be positioned in a knee joint as the wearer's joint whereby the elastic cross strap provides the resistance force to the extension of the upper mounting facility and the lower mounting facility from the cross origin when the cross origin is positioned in the popliteal fossa of the knee joint.

12. The elastic brace assembly of claim 1 wherein the elastic brace assembly further provides patella control.

13. The elastic brace assembly of claim 1 wherein the elastic brace assembly provides a structure for patella control.

14. A hyperextension brace assembly comprising:
an upper mounting facility capable of securing a brace on a user's first limb about a joint;
a lower mounting facility capable of securing the brace on a user's second limb about the joint;
a cross strap having at least two arms attachable to the upper mounting facility and the lower mounting facility;
the cross strap configured to form a cross origin in a fossa of the wearer's joint;
at least one of the at least two arms capable of extending from the lower mounting facility laterally to a position posterior to the joint and continuing medial to the upper mounting facility; and
at least one of the at least two arms capable of extending from the lower mounting facility medially to a position posterior to the joint and continuing lateral to the upper mounting facility whereby the cross strap is capable of limiting an extension of the user's first and the user's second limb about the joint.

15. The hyperextension brace assembly of claim 14 wherein the cross strap is capable of limiting the extension without the use of a hinge about the joint.

16. The hyperextension brace assembly of claim 14 wherein:
the upper mounting facility having an upper mount front portion;
the lower mounting facility having a lower mount front portion;
an upper portion of at least one of the at least two arms connect to the upper mounting facility at an upper attachment point on the upper mount front portion and a lower portion of at least one of the two arms connect to the lower mounting facility at a lower attachment point on the lower mount front portion; and
the cross strap limits the extension of the user's joint by limiting the extension of the upper mount front portion and the lower mount front portion relative to a cross origin.

17. The hyperextension brace assembly of claim 14 wherein the upper mounting facility and the lower mounting facility are operably connected by a flexible upright.

18. The elastic brace assembly of claim 14 wherein the elastic brace assembly further provides patella control.

19. The elastic brace assembly of claim 14 wherein the elastic brace assembly provides a structure for patella control.

20. An elastic brace assembly for use by a wearer, the elastic brace assembly comprising:
an upper mounting facility and a lower mounting facility;
at least one elastic cross strap coupled to the upper mounting facility and the lower mounting facility;
the at least one elastic cross strap further forming a cross origin between the upper mounting facility and the lower mounting facility whereby the elastic cross strap provides a resistance force to an extension of the upper mounting facility and the lower mounting facility from the cross origin when the cross origin is positioned in a fossa of a wearer's joint;
the elastic cross strap comprises a single strap capable of being woven about a leg of the wearer to create the upper mounting facility, the lower mounting facility and an x-pattern as the cross origin;
the upper mounting facility formed by a first wrap of the elastic cross strap around the leg of the wearer;
the lower mounting facility formed by a second wrap of the elastic cross strap around the leg of the wearer;
the cross origin formed by at least a third wrap of the elastic cross strap around the leg of the wearer; and
the elastic brace assembly providing the resistance force to the extension without the use of a hinge.

21. The elastic brace assembly of claim 20 wherein:
the elastic cross strap comprises a substantially elastic material;
the cross origin is configured to be positioned in the fossa of the wearer's joint; and
the elastic cross strap is configured to provide a dynamic resistance force as the resistance force.

22. The elastic brace assembly of claim 20 wherein the upper mounting facility and the lower mounting facility are operably connected by a flexible upright.

\* \* \* \* \*